US009211512B2

(12) United States Patent
Kim et al.

(10) Patent No.: US 9,211,512 B2
(45) Date of Patent: Dec. 15, 2015

(54) MICROFLUIDIC APPARATUS AND METHOD OF ENRICHING TARGET CELLS BY USING THE SAME

(71) Applicant: Samsung Electronics Co., Ltd., Suwon-si, Gyeonggi-do (KR)

(72) Inventors: Min Seok S. Kim, Yongin-si (KR); Jong-myeon Park, Incheon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/026,805

(22) Filed: Sep. 13, 2013

(65) Prior Publication Data
US 2014/0147862 A1 May 29, 2014

(30) Foreign Application Priority Data
Nov. 28, 2012 (KR) .......................... 10-2012-0136552

(51) Int. Cl.
*B01F 11/02* (2006.01)
*B01F 11/00* (2006.01)
(Continued)

(52) U.S. Cl.
CPC ........... *B01F 11/002* (2013.01); *B01F 13/0059* (2013.01); *B01L 3/50273* (2013.01); *B01L 3/502746* (2013.01); *B01L 3/502753* (2013.01); *B01L 2300/0803* (2013.01);
(Continued)

(58) Field of Classification Search
USPC ........................................................ 436/177
See application file for complete search history.

(56) References Cited

U.S. PATENT DOCUMENTS 5,143,630 A 9/1992 Rolchigo
6,632,399 B1 * 10/2003 Kellogg et al. ................. 422/72
(Continued)

FOREIGN PATENT DOCUMENTS

EP 1900432 a2 3/2008
EP 2026074 a2 2/2009
(Continued)

OTHER PUBLICATIONS

Beom Seok Lee, Jung-Nam Lee, Jong-Myeon Park, Jeong-Gun Lee, Suhyeon Kim, Yoon-Kyoung Cho and Christopher Ko "A fully automated immunoassay from whole blood on a disc" Lab Chip, 2009, 9, 1548-1555.*
(Continued)

*Primary Examiner* — Christopher A Hixson
*Assistant Examiner* — Emily Berkeley
(74) *Attorney, Agent, or Firm* — Leydig, Voit & Mayer, Ltd.

(57) ABSTRACT

A microfluidic apparatus capable of being mounted on a rotation driving unit. When mounted on the rotation driving unit and rotated, a fluid flow is induced in the apparatus due to a centrifugal force. the microfluidic apparatus includes a sample supplying unit that comprises a sample chamber to house a sample and provides a fluid including a target material in which fine beads are bound to a target cell in the sample; a density-gradient separation unit that houses a density gradient material with a lower density than the target material, and receives the fluid from the sample supplying unit to separate the target material from the fluid based on a density difference; a fluid supplying channel connecting the sample supplying unit to the density-gradient separation unit to form a passage of the fluid; and a fluid supplying valve provided to the fluid supplying channel to selectively allow a flow of the fluid.

21 Claims, 14 Drawing Sheets

(51) Int. Cl.
  *B01L 3/00* (2006.01)
  *B01F 13/00* (2006.01)
  *G01N 21/03* (2006.01)
  *G01N 21/64* (2006.01)
  *G01N 15/14* (2006.01)

(52) U.S. Cl.
  CPC ... *B01L 2300/087* (2013.01); *B01L 2300/0864* (2013.01); *B01L 2400/0409* (2013.01); *B01L 2400/0677* (2013.01); *B01L 2400/084* (2013.01); *G01N 21/03* (2013.01); *G01N 21/6428* (2013.01); *G01N 2015/149* (2013.01)

(56) References Cited

U.S. PATENT DOCUMENTS

| | | | | |
|---|---|---|---|---|
| 7,857,141 | B2* | 12/2010 | Park et al. | 209/199 |
| 2008/0058991 | A1* | 3/2008 | Lee et al. | 700/266 |
| 2008/0290048 | A1 | 11/2008 | Jaeggi et al. | |
| 2010/0233694 | A1* | 9/2010 | Kopf-Sill | 435/6 |
| 2011/0020194 | A1* | 1/2011 | Lee et al. | 422/400 |

FOREIGN PATENT DOCUMENTS

| | | |
|---|---|---|
| JP | 2006-505766 A | 2/2006 |
| KR | 1020000048669 A | 7/2000 |
| KR | 1020100121333 A | 11/2010 |

OTHER PUBLICATIONS

Cho et al., "One-step pathogen specific DNA extraction from whole blood on a centrifugal microfluidic device," *Lab Chip* 7: 565-573 (2007).

Gorkin et al., "Centrifugal microfluidics for biomedical applications," *Lab Chip* 10: 1758-1773 (2010).

Lee et al., "A fully automated immunoassay from whole bold on a disc," *Lab Chip* 9: 1548-1555 (2009).

Park et al., "Multifunctional microvalves control by optical illumination on nanoheaters and its application in centrifugal microfluidic devices," *Lab Chip* 7: 557-564 (2007).

Park et al., "Lab-on-a-Disc for Fully Integrated Multiplex Immunoassays," *Analytical Chemistry* 84: 2133-2140 (2012).

European Patent Office, Extended European Search Report in European Patent Application No. 13190672.9, Mar. 6, 2014, 4 pp.

* cited by examiner

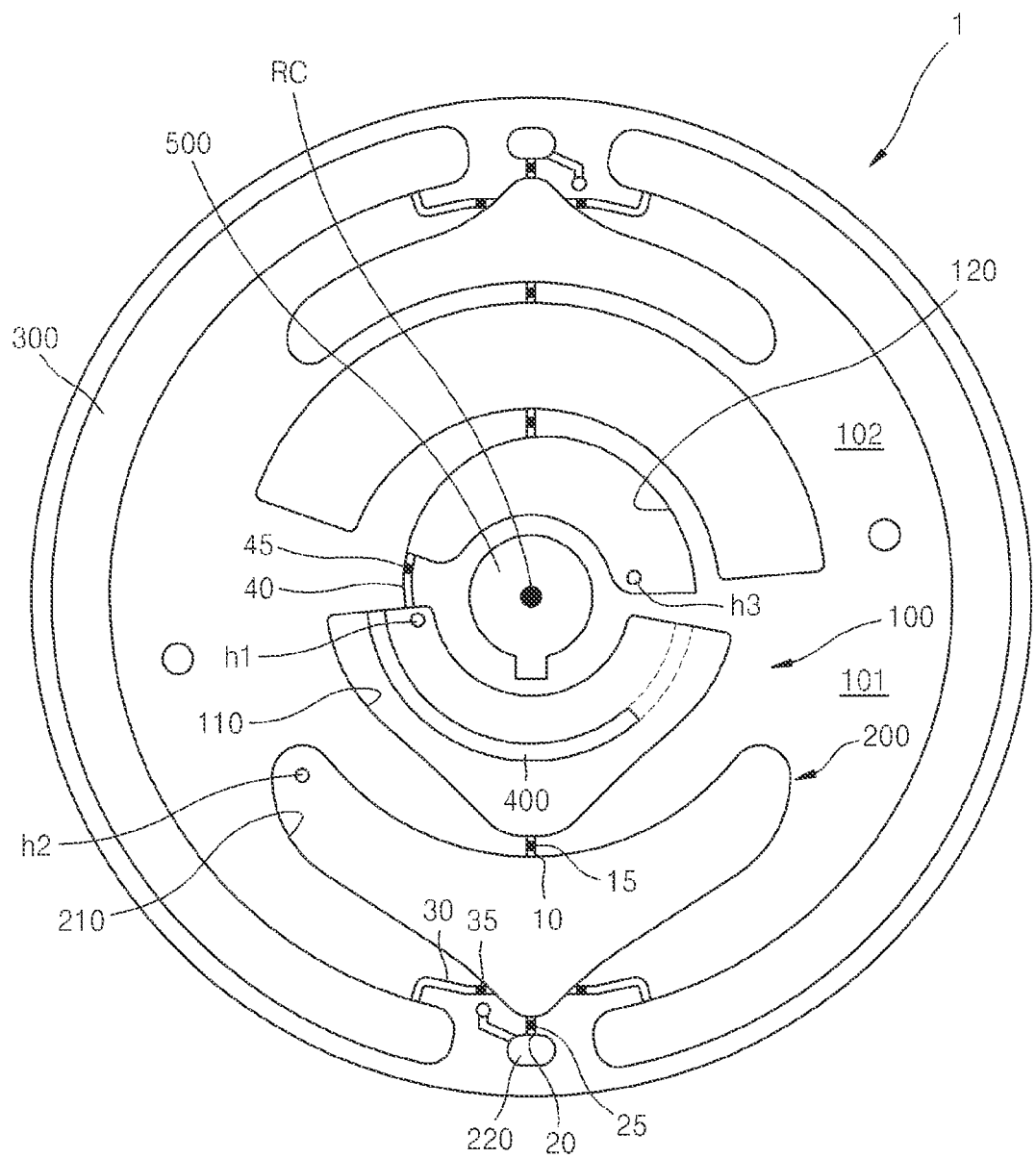

MICROFLUIDIC APPARATUS AND METHOD OF ENRICHING TARGET CELLS BY USING THE SAME

CROSS-REFERENCE TO RELATED APPLICATIONS

This application claims the benefit of Korean Patent Application No. 10-2012-0136552, filed on Nov. 28, 2012, in the Korean Intellectual Property Office, the disclosure of which is incorporated herein in its entirety by reference.

BACKGROUND

1. Field

The present disclosure relates to microfluidic apparatuses for isolating target cells in a biological sample and methods of enriching target cells by using the microfluidic apparatuses.

2. Description of the Related Art

Death of a patient caused by a malignant tumor is mostly due to metastasis of the tumor from a site where the tumor originally occurred to other tissues or organs. Accordingly, in order to increase the chance of survival for a cancer patient, it is very important to discover tumor metastasis early; early discovery of the tumor and monitoring the growth of the tumor are regarded as major elements for successful treatment of the patient. In general, cancer is diagnosed by histopathology. Histopathology is a diagnosis method wherein a tissue sample obtained from a biopsy specimen is used to directly identify tumor cells. However, a tissue selected to obtain a biopsy specimen sample may not contain a tumor, and since only data about a particular site obtained from the biopsy specimen is provided, identifying metastasis of a tumor to other sites is quite limited. Accordingly, use of histopathology in diagnosing or monitoring tumors has many limitations.

Circulating tumor cells (CTCs) can be identified in patients before a tumor is originally detected, and CTCs may play an important factor in diagnosing cancer early. In addition, since cancer spreads through blood in most cases, CTCs may be used as a marker for identifying cancer metastasis. In addition, CTCs can be detected even after cancer cells are removed by a surgical operation, and in this case, the possibility of recurrence of cancer is very high. However, since the amount of CTCs in blood may be very small (for example few CTC cells per mL of blood) and the CTCs are very fragile, it is difficult to correctly identify the number of CTCs. Accordingly, there is a need to develop a diagnosis method with high sensitivity in detecting CTCs, cancer cells, or cancer stem cells present in the body of patients. In order to obtain a sufficient amount of CTC cells for an accurate detection, an apparatus which can process a relatively large amount of blood (for example up to about 20 mL) is needed as well.

Red blood cells, white blood cells/circulating tumor cells, or a serum may be manually separated from a density gradient in order to isolate CTCs, cancer cells, or cancer stem cells. However, layer of white blood cells/circulating tumor cells is very thin, and thus, manually separating the layer of white blood cells/circulating tumor cells based on the density gradient is difficult and also separation reproducibility largely depends on the ability of the person who performs the separation.

SUMMARY

Provided are microfluidic apparatuses for separating and enriching target cells in a biological sample according to an automated process, and methods of enriching target cells by using the microfluidic apparatuses.

Additional aspects will be set forth in part in the description which follows and, in part, will be apparent from the description, or may be learned by practice of the presented embodiments.

According to an aspect, a microfluidic apparatus is provided that is adapted to be mounted on a rotation driving unit and wherein when mounted on the rotation driving unit and rotated about a rotation center of the apparatus, a fluid flow is induced in the apparatus due to a centrifugal force. The microfluidic apparatus typically includes a sample chamber in which a sample fluid is centrifuged, wherein a partition wall is provided in the sample chamber to form a bottleneck portion together with at least one of a top wall and a bottom wall of the sample chamber to partially restrict the flow of the sample fluid in a radial direction of the sample chamber, and wherein a gap between the bottleneck portion and the at least one of the top wall and the bottom wall has a size or dimension that is greater than a size or dimension of a gap that would induce a capillary phenomenon with the sample fluid and which is sufficiently large to allow target cells and fine beads in the sample fluid to move back and forth through the gap during a mixing process whereby the apparatus is rotated back and forth in clockwise and counterclockwise directions, and which partially restricts the flow of sample fluid in an inward radial direction when the apparatus is not being rotated.

The partition wall may have such a shape that the bottleneck portion is narrower from an inner portion of the sample chamber to an outer portion of the sample chamber in the radial direction of the sample chamber.

The partition wall may be formed across a width of the sample chamber in a circumference direction of the sample chamber.

The partition wall may be formed across a portion of a width of the sample chamber in a circumference direction of the sample chamber.

A plurality of the partition walls may be arranged in a circumference direction of the sample chamber and the partition walls are spaced apart from each other with an opening between adjacent partition walls.

Each of the openings may be narrower from an inner portion of the sample chamber to an outer portion of the sample chamber in the radial direction.

According to another aspect, a method of enriching a target cell using a microfluidic apparatus that induces a flow of a fluid housed therein due to a centrifugal force is provided. The method typically includes forming a target material comprising target cells bound to fine beads that specifically connect to a surface marker of the target cell by mixing a sample containing the target cell with the fine beads in a sample chamber of the microfluidic apparatus, said sample chamber having a partition wall that forms a bottleneck portion together with at least one of a top wall and a bottom wall of the sample chamber, wherein a gap between the bottleneck portion and the at least one of the top wall and the bottom wall has a size or dimension that is greater than a size or dimension of a gap that would induce a capillary phenomenon and which is sufficiently large to allow the target material, and target cells and fine beads, to move back and forth through the gap during mixing and which partially restricts the flow of fluid in an inward radial direction after mixing. The method also typically includes transporting a fluid comprising the target material through a fluid supplying channel to a separation chamber housing a density gradient material having a density lower than that of the target material and higher than that of the fluid, and separating the target material from the fluid based on a density difference due to a centrifugal force applied in the separation chamber upon rotating the microfluidic apparatus, thereby enriching the target material.

Separating may include separating the target material from the fluid with the density gradient material interposed therebetween in the separation chamber due to centrifugation, and recovering the target material into a recovery chamber through a recovery channel.

Forming the target material may include centrifuging the sample into a plurality of layers including a target layer comprising the target cell and an upper material layer located above the target layer due to a centrifugal force in the sample chamber, before the fine beads are introduced into the sample chamber, discharging the upper material layer into a waste chamber through a second channel, introducing the fine beads into the sample chamber through a first channel, and forming the target material in which the target cell is bound to the fine beads.

In certain aspects, the method includes, after discharging, closing the second channel.

Forming of the target material further may include supplying the fine beads with a buffer to the sample chamber, locating the buffer above the target layer by centrifugation, opening the second channel to discharge the buffer to the waste chamber through the second channel, and closing the second channel.

Forming the target material, before the fine beads are introduced into the sample chamber, may further include supplying a lysis solution to the sample chamber to lyse a particular cell in the sample.

In certain aspects, the target cell includes a circulating tumor cell, a cancer stem cell, or a cancer cell.

According to another aspect, a method of enriching a target cell using a microfluidic apparatus that induces a flow of a fluid housed therein due to a centrifugal force is provided. The method typically includes housing a sample comprising a target cell and a first density gradient material with a density higher than that of the target cell in a sample chamber of the microfluidic apparatus, centrifuging the sample to locate a target layer comprising the target cell above the first density gradient material layer, transporting the target layer from the sample chamber to a reaction chamber, mixing the target layer with fine beads that specifically bind to a surface marker of the target cell in a reaction chamber to form a target material in which the fine beads are bound to the target cell, said reaction chamber having a partition wall that forms a bottleneck portion together with at least one of a top wall and a bottom wall of the reaction chamber, wherein a gap between the bottleneck portion and the at least one of the top wall and the bottom wall has a size or dimension that is greater than a size or dimension of a gap that would induce a capillary phenomenon and which is sufficiently large to allow the target material, and the target cells and fine beads, to move back and forth through the gap during mixing and which partially restricts the flow of fluid in an inward radial direction after mixing, transporting a fluid comprising the target material to a separation chamber housing a density gradient material with a density lower than that of the target material and higher than the fluid through the fluid supplying channel, and separating the target material from the fluid based on a density difference due to a centrifugal force applied in the separation chamber upon rotating the microfluidic apparatus, thereby enriching the target material.

In certain aspects, the target cell includes a circulating tumor cell, a cancer stem cell, or a cancer cell.

According to yet another aspect, a microfluidic apparatus is provided that is adapted to be mounted on a rotation driving unit and wherein when mounted on the rotation driving unit and rotated about a rotation center of the apparatus, a fluid flow is induced in the apparatus due to a centrifugal force. The microfluidic apparatus typically includes a sample supplying unit having a sample chamber that houses a sample fluid including a fluid and a target material in which fine beads are bound to a target cells in the sample fluid, a density-gradient separation unit that houses a density gradient material with a lower density than the target material, wherein the density-gradient separation unit is located farther away along a radial direction from the rotation center than the sample chamber, a fluid supplying channel that fluidly couples the sample supplying unit with the density-gradient separation unit, and a fluid supplying valve in the fluid supplying channel to selectively allow a flow of the sample fluid through the fluid supplying channel, wherein the density-gradient separation unit receives the sample fluid from the sample supplying unit and the target material is separated from the fluid based on density difference.

The sample chamber typically includes a partition wall that forms a bottleneck portion together with at least one of a top wall and a bottom wall of the sample chamber to partially restrict the flow of the sample fluid in a radial direction of the sample chamber, and wherein a gap between the bottleneck portion and the at least one of the top wall and the bottom wall has a size or dimension that is greater than a size or dimension of a gap that would induce a capillary phenomenon and which is sufficiently large to allow target cells and fine beads in the sample fluid to move back and forth through the gap during a mixing process whereby the apparatus is rotated back and forth in clockwise and counterclockwise directions, and which partially restricts the flow of sample fluid in an inward radial direction when the apparatus is not being rotated.

The size or dimension of the gap is typically between about 0.5 mm and about 20.0 mm.

The partition wall typically has a shape wherein the bottleneck portion is narrower from an inner portion of the sample chamber to an outer portion of the sample chamber in the radial direction of the sample chamber.

The partition wall is typically formed across a width of the sample chamber in a circumference direction of the sample chamber.

The partition wall may be formed across a portion of a width of the sample chamber in a circumference direction of the sample chamber.

In certain aspects, a plurality of the partition walls are arranged in a circumference direction of the sample chamber and wherein the partition walls are spaced apart from each other with an opening between adjacent partition walls.

In certain aspects, each of the openings is narrower from an inner portion of the sample chamber to an outer portion of the sample chamber in the radial direction.

The density-gradient separation unit may include a separation chamber that is connected to the sample chamber by the fluid supplying channel and houses the density gradient material, a recovery chamber that is connected to the separation chamber by a recovery channel and recovers the target material from the separation chamber, and a recovery valve that is provided to the recovery channel to control a flow of the fluid.

The microfluidic apparatus may include a waste chamber; a discharge channel that is disposed more inside than the recovery channel in the radial direction and connects the separation chamber to the waste chamber, to discharge a portion of the fluid disposed above the target material from the separation chamber; and a discharge valve that is provided to the discharge channel to control the flow of the fluid.

The sample supplying unit may include a fine bead chamber housing the fine beads, a first channel connecting the sample chamber to the fine bead chamber, and a first valve provided to the first channel to selectively allow a flow of the fine beads into the sample chamber, and the density-gradient separation unit is connected to the sample chamber.

The sample is separated into a plurality of layers due to a centrifugal force in the sample chamber, and the layers includes a target layer including the target cell and an upper material layer located above the target layer, and the microfluidic apparatus may further include a waste chamber; a second channel connecting the sample chamber to the waste chamber; and a second valve for selectively opening the second channel, wherein the upper material layer is discharged to the waste chamber through the second channel.

A third valve may be further provided in the second channel and is located more closer to the waste chamber than the second valve, so that when the upper material layer is discharged, the third valve closes the second channel.

A fourth valve may be further provided in the second channel to sequentially close and open the second channel.

The microfluidic apparatus may further include a lysis solution chamber for providing a lysis solution to lyse a particular cell in the sample.

The sample chamber may house the sample and a first density gradient material, and due to a centrifugal force, a target layer including the target cell is located above the first density gradient material, and the sample supplying unit further includes a reaction chamber that receives the fluid including the target layer from the sample chamber so that the fluid is mixed with the fine beads to form the target material.

The target cell may be a circulating tumor cell, a cancer stem cell, or a cancer cell.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

These and/or other aspects will become apparent and more readily appreciated from the following description of the embodiments, taken in conjunction with the accompanying drawings of which:

FIG. 3 is a plan view of a microfluidic apparatus including a particle chamber, according to an embodiment;

DETAILED DESCRIPTION

Figure 1A:
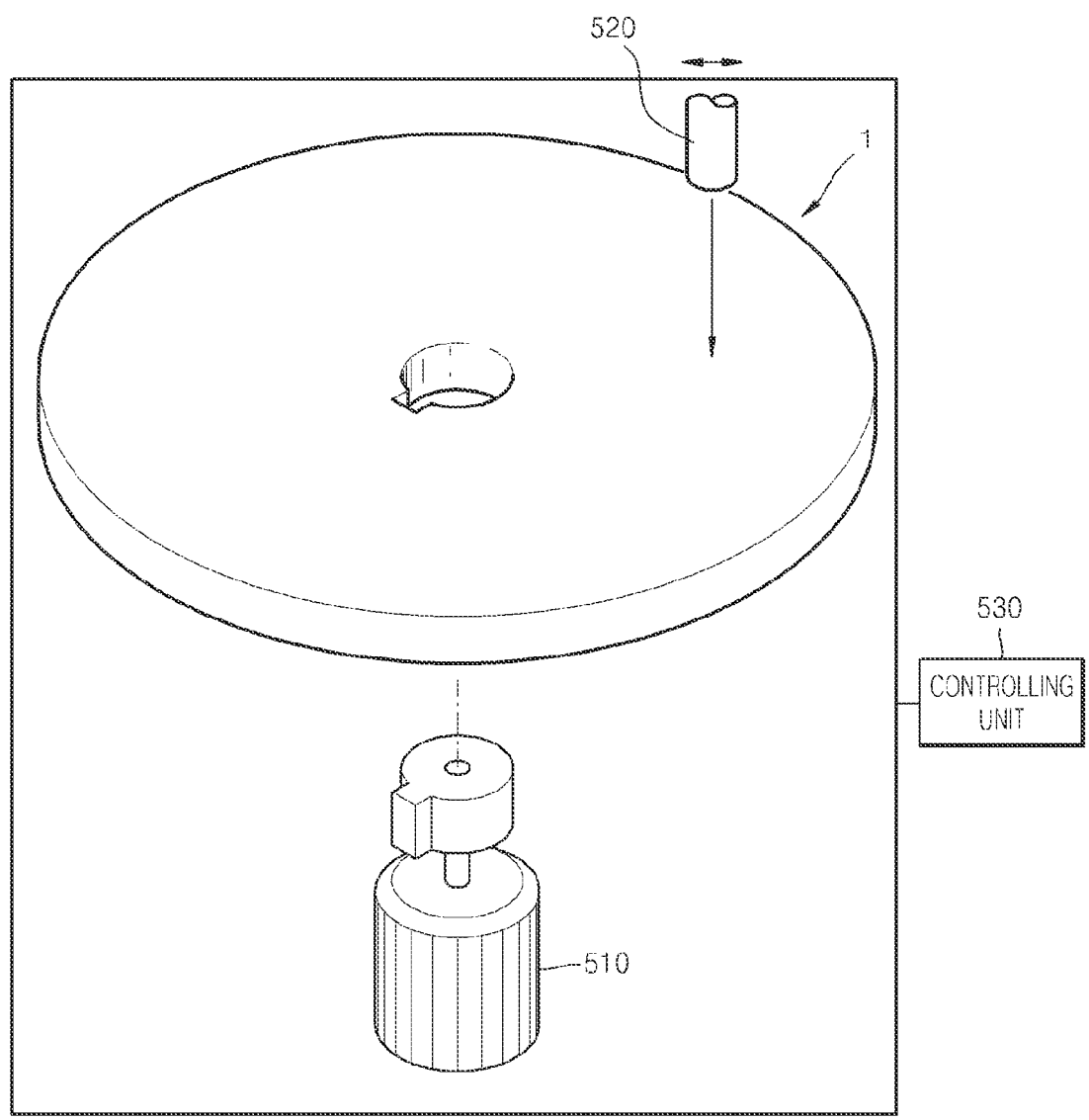
FIG. 1A is a schematic diagram of a cell enrichment system according to an embodiment.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify each element of the list.

Hereinafter, embodiments are described in detail with reference to the attached drawings. These embodiments are presented herein for illustrative purpose only, and the scope is not limited thereto.

FIG. 1A illustrates an example of a cell enrichment system including a microfluidic apparatus 1 according to an embodiment. FIG. 1A illustrates a rotation driving unit 510 and an electromagnetic wave generator 520. The rotation driving unit 510 rotates the microfluidic apparatus 1 to provide a centrifugal force for centrifugating a sample and moving a fluid. The rotation driving unit 510 may stop the microfluidic apparatus 1 from rotating at a predetermined location so that specific valves of microfluidic apparatus 1 face the electromagnetic wave generator 520. The electromagnetic wave generator 520 is used to operate the valves of the microfluidic apparatus 1, and for example, the electromagnetic wave generator 520 irradiates the valve, e.g., using a laser beam. The electromagnetic wave generator 520 may move in a radial direction of the microfluidic apparatus 1. Although not illustrated in FIG. 1, the rotation driving unit 510 may include a motor drive apparatus that controls an angular position of the microfluidic apparatus 1 to align the valves of the microfluidic apparatus 1 and the electromagnetic wave generator 520. For example, the motor drive apparatus may include a step motor or a direct current motor. A reference numeral 530 denotes a controlling unit for controlling operation of the driving unit 510 and electromagnetic wave generator 520, and also for controlling operation of an enriching process as will be described with reference to various embodiments below.

Figure 1B:
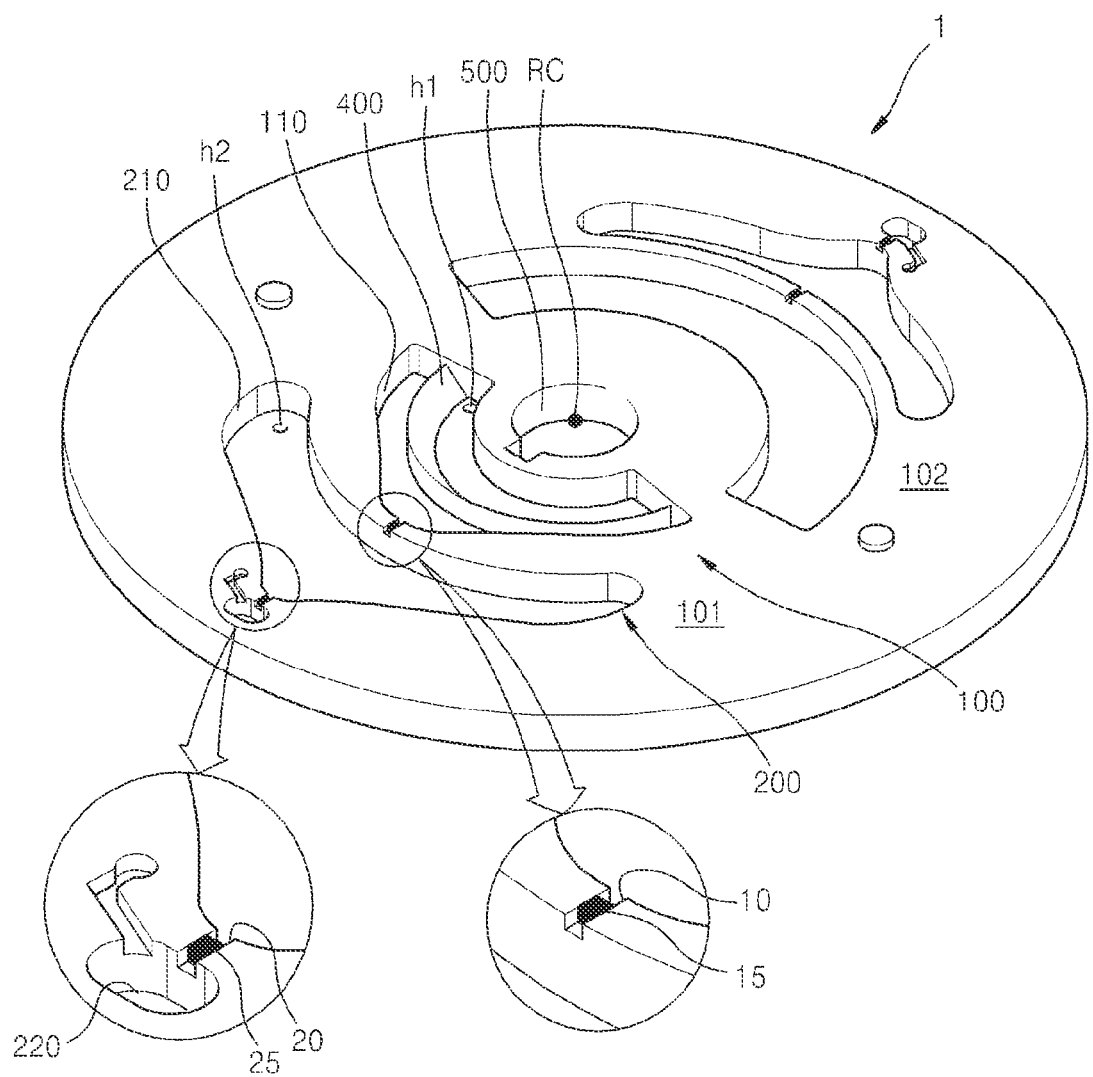
FIG. 1B is a perspective view of a microfluidic apparatus according to an embodiment from which a top plate is removed.

FIG. 1B is a perspective view of the microfluidic apparatus 1 not including a top (cover) plate. The microfluidic apparatus 1 according to the present embodiment, when rotated, induces flow of a fluid housed therein due to a centrifugal force. The microfluidic apparatus 1 includes a microfluidic structure for providing a space for housing a fluid and a passage of the fluid. The microfluidic apparatus 1 may have, for example, a rotatable disc shape as shown, but is not limited thereto, and may take on other shapes as may be well known or desired.

The microfluidic apparatus 1 may be formed of a plastic material that is moldable and has a biologically inactive surface. Examples of such plastic material include acryl and PDMS. However, the material for the microfluidic apparatus 1 is not limited thereto, and may include one or more of various materials that have desirable properties such as chemical and biological stability, optical transparency, and mechanical processability. The microfluidic apparatus 1 may include a plurality of plates. A concave structure corresponding to a chamber or a channel is formed at a contact surface of the plates, and then, the plates are combined to form a space for housing a fluid and a passage for the fluid inside the microfluidic apparatus 1. For example, the microfluidic apparatus 1 may have a double-plate structure including a top plate and a bottom plate wherein the microfluidic structure elements, e.g., various spaces, chambers and passageways/channels, are formed in the top and/or bottom plate according to an embodiment. However, according to another embodiment, the microfluidic apparatus 1 may have a triple-plate structure including a top plate, a bottom plate, and a partition plate defining the microfluidic structure. The plates may be combined by using an adhesive or a double-side adhesive tape, or by ultrasonic wave fusing or laser fusing or otherwise as would be apparent to one skilled in the art.

The microfluidic apparatus 1 may have a single microfluidic structure or a plurality of microfluidic structures. For example, the microfluidic apparatus 1 may be divided into a plurality of regions, each of which may include a microfluidic structure that operates independently of the other structures, or a microfluidic structure may interoperate with one or more other microfluidic structures. For example, the microfluidic apparatus 1 according to the present embodiment includes two regions 101 and 102, each including a microfluidic structure. The microfluidic structure of the regions 101 and 102 may have a substantially identical structure, and thus, hereinafter, only the microfluidic apparatus 1 of the region 101 is described in detail.

The microfluidic apparatus 1 may have a mounting portion 500 at its rotation center RC for placement on and attachment to the rotation driving unit 510. A sample supplying unit 100 and a density-gradient separation unit 200 are provided in a radial direction from the rotation center RC, that is, in a direction of the resulting centrifugal force. The sample supplying unit 100 and the density-gradient separation unit 200 are connected to each other by fluid supplying channel 10. A fluid supplying valve 15 is provided in the fluid supplying channel 10 to control the flow of a fluid through channel 10.

The sample supplying unit 100 is provided to house or store a fluid including a target material, e.g., a target cell-fine beads complex. In the sample supplying unit 100, a target cell included in a sample contacts fine beads and the fine beads attach to the target cell to form a target cell-fine beads complex. The fine beads may include, for example, solid fine beads, magnetic beads, gel beads, polymer fine beads, or the like. According to an embodiment, the sample supplying unit 100 includes a sample chamber 110 for housing a sample and fine beads. The sample chamber 110 may have an inlet port h1 for loading a sample. The fine beads may be loaded into the sample chamber 110 through the inlet h1 before a target cell is enriched. The inlet h1 illustrated in FIG. 1B may alternatively be provided in the top plate. According to another embodiment, when the microfluidic apparatus 1 is manufactured for a predetermined task, fine beads suitable for the task may be housed in advance in the sample chamber 110, e.g., introduced during the procedure of manufacturing the microfluidic apparatus 1. A partition wall 400 is provided in the sample chamber 110 to at least partially restrict the flow of a fluid in the radial direction in certain embodiments. The partition wall 400 will be described below in connection with FIGS. 11 to 14.

The density-gradient separation unit 200 is provided to separate a target material from a fluid including the target material provided by the sample supplying unit 100. The density-gradient separation unit 200 includes a separation chamber 210 accommodating a density-gradient material (DGM). The DGM is provided to separate a target material from a fluid including the target material based on a density gradient. A density of the DGM should be lesser than that of the target material and greater than that of the fluid other than the target material. Due to the density difference, during centrifugation, the DGM will be located between the fluid and the target material so as to separate the target material from the fluid. An inlet port h2 may be provided in the separation chamber 210 to load the DGM. The inlet h2 may instead be provided in the top plate. When the microfluidic apparatus 1 is to be used for a particular task, the DGM suitable for the task can be housed in the separation chamber 210 in advance, e.g., introduced during the procedure of manufacturing the microfluidic apparatus 1.

To make the fluid flow from the sample chamber 110 to the separation chamber 210 due to the centrifugal force, the separation chamber 210 is disposed outside of the sample chamber 110 in the radial direction away from the rotation center RC. The sample chamber 110 and the separation chamber 210 are connected to each other by the fluid supplying channel 10, which includes the fluid supplying valve 15. In the separation chamber 210, the target material is separated from the fluid with the DGM interposed therebetween. The target material may gather in the lowest layer of the separation chamber 210, that is, the most outside material layer in the radial direction away from the rotation center RC. An extraction hole (not shown) may be provided in the separation chamber 210 to extract a target material. The extraction hole may be provided in an outer region of the separation chamber 210 in the radial direction. For example, the target material in the lowest layer is extracted through an extraction hole, e.g., by using a pipette, thereby separating the target material from the sample. By doing so, target cells existing in a very small amount in a sample may be efficiently separated and enriched.

The density-gradient separation unit 200 may further include a recovering chamber 220 for housing a target material. The recovery chamber 220 is disposed outside the separation chamber 210 in the radial direction away from the rotation center RC. The recovery chamber 220 is connected to the separation chamber 210 by a recovery channel 20. A recovery valve 25 is provided in the recovery channel 20 to selectively control fluid flow through channel 20. In the separation chamber 210, the target material gathers in the lowest layer of the separation chamber 210, and when the recovery channel 25 is open by the recovery valve 25, the target material flows into the recovery chamber 25 due to a centrifugal force. As used herein "lowest layer" is meant to refer to the material layer farthest away from the rotation center RC, e.g., the heaviest material in a mixture will gather farthest away from the RC during centrifugation; similarly "highest layer" is meant to refer to the material layer closest to the rotation center RC, e.g., the lightest material will gather closest to the RC during centrifugation.

Figure 1C:
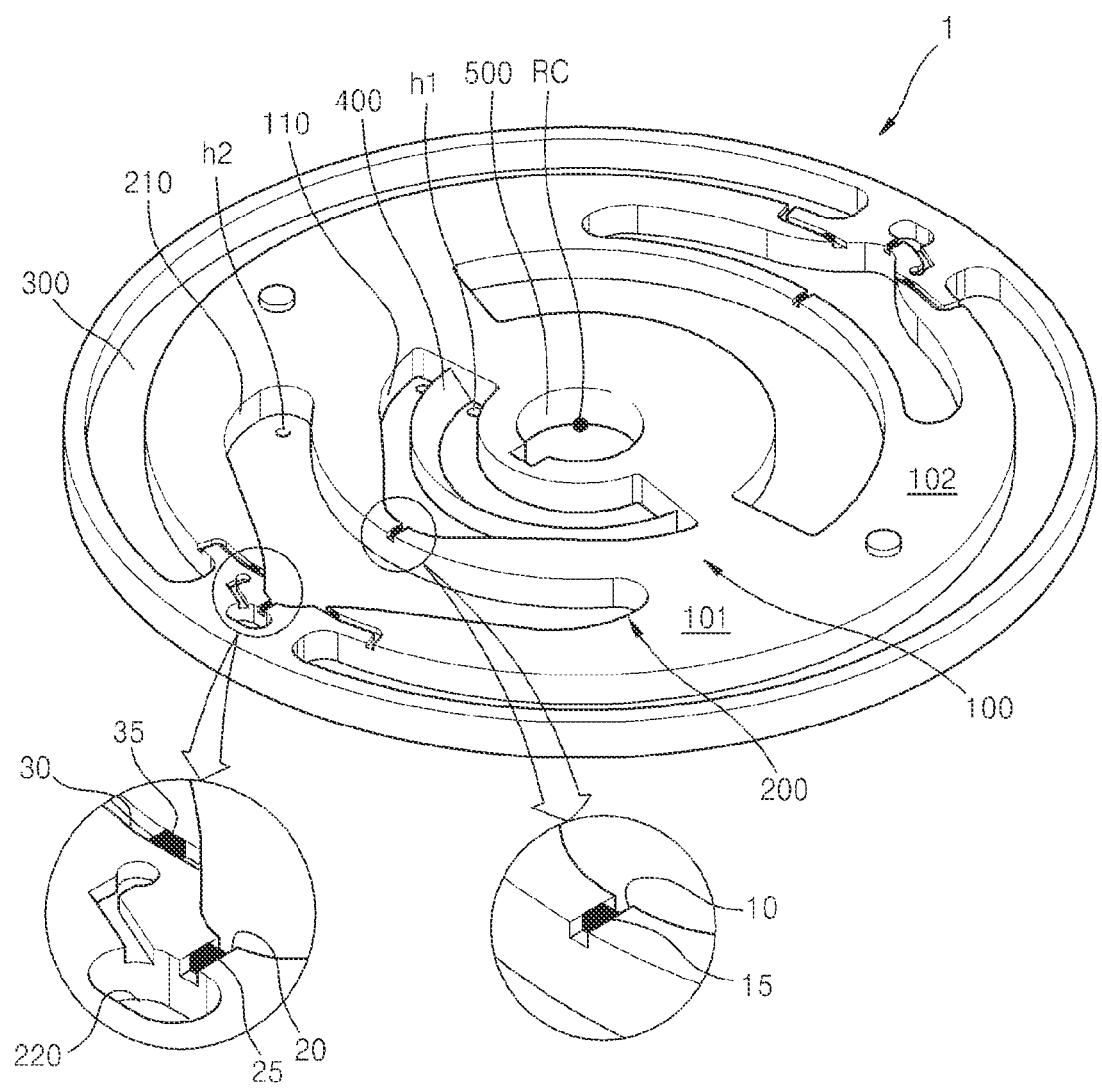
FIG. 1C is a perspective view of the microfluidic apparatus of FIG. 1B further including a waste chamber according to an embodiment.

Referring to FIG. 1C, a waste chamber 300 is also provided in the microfluidic apparatus 1 in certain embodiments. The separation chamber 210 may be connected to the waste chamber 300 by one or more discharge channels 30. A discharge channel 30 may be connected to the separation chamber 210 such that the discharge channel 30 is closer to the rotation center RC than the recovery channel 20. A discharge valve 35 may be provided in the discharge channel 30 to selectively control the flow of a fluid through channel 30. Due to such a structure, a material in upper layers other than the target material in the lowest layer of the separation chamber 210 is discharged to the waste chamber 300 through the discharge channel 30, and the target material may be moved to the recovery chamber 220 through the recovery channel 220.

Figure 2A:
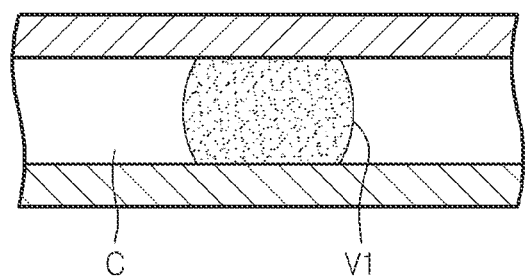
FIGS. 2A and 2B are cross-sectional views of a normally closed valve according to an embodiment.
Figure 2B:
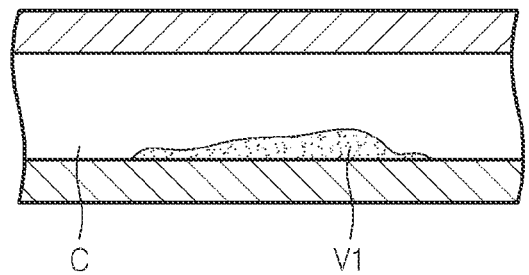

Various types of microfluidic valves may be used as the fluid supplying valve 15, the recovery valve 25, the discharge valve 35 and any other valves as may be included in the microfluidic apparatus 1. The fluid supplying valve 15, the recovery valve 25, and the discharge valve 35 are, in certain embodiments, normally closed valves that prevent the flow of a fluid until activated, e.g., until they receive energy from the outside, to open. FIGS. 2A and 2B illustrate an example of a normally closed valve and the valve in an open state, respectively. The normally closed valve may include a valve material V1 that is in a solid state at room temperature and thus clogs a channel C as illustrated in FIG. 2A. The valve material V1 melts at high temperature and moves within the channel C, and as illustrated in FIG. 2B, the valve material V1 returns to the solid state while the channel C is being opened. Energy irradiated from the outside may include, for example, an electromagnetic wave, and an energy source may include a laser beam source that irradiates with a laser beam, a light emitting diode that irradiates visible light or infrared light, or an Xenon lamp. When a laser beam source is used, the laser beam source may include at least one laser diode. The energy source may be selected according to a wavelength of an electromagnetic wave that is absorbable by exothermic particles included in the valve material V1. Valve material V1 may include a thermoplastic resin, such as a cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU), or polyvinylidene fluoride (PVDF), a phase change material that exists in a solid state at room temperature may be used. The phase change material may be wax. When heated, wax dissolves into a liquid state and a volume thereof expands. Examples of the wax are paraffin wax, microcrystalline wax, synthetic wax, and natural wax. The phase change material may be a gel or a thermoplastic resin. Examples of useful gel materials include polyacrylamides, polyacrylates, and polymethacrylates. A plurality of fine exothermic particles that absorb electromagnetic wave energy and emit heat may be dispersed in the valve material V1. Fine exothermic particles may have an average particle size of about 1 nm to about 100 µm to freely pass the fine channel C having a depth of about 0.1 mm and a width of about 1 mm. Fine exothermic particles may have an exothermic property, and thus, when electromagnetic wave energy is supplied by, for example, exposure to laser light, a temperature thereof increases rapidly, and the fine exothermic particles may homogeneously disperse in wax. To obtain such a property, each of the fine exothermic particles may have a core including a metallic component and a hydrophobic surface structure. For example, the fine exothermic particles may each have a molecular structure in which a plurality of surfactants are bound to and cover a Fe-core. The fine exothermic particles may be preserved in a dispersion state in carrier oil. The carrier oil may also be hydrophobic to allow the fine exothermic particles having a hydrophobic surface structure to be homogeneously dispersed.

Carrier oil with the fine exothermic particles dispersed therein is mixed with a molten phase change material, and the mixture is loaded into the channel C and solidified to clog the channel C. The fine exothermic particles are not limited to the polymer particles presented as an example of the fine exothermic particles, and quantum dots or magnetic beads may also be used as fine exothermic particles. In addition, the fine exothermic particles may include, for example, a fine metal oxide, such as $Al_2O_3$, $TiO_2$, $Ta_2O_3$, $Fe_2O_3$, $Fe_3O_4$, or, $HfO_2$. In addition, no fine exothermic particles may be necessarily included in the normally closed valve, and according to another embodiment, the normally closed valve may be a phase change material without any fine exothermic particles.

The target cell may include a circulating tumor cell (CTC), a cancer stem cell, or a cancer cell. The target cell may include, for example, a cancer or tumor cell selected from the group consisting of bladder cancer, breast cancer, uterine cervical cancer, cholangiocarcinoma, colorectal cancer, uterine endometrial cancer, esophageal cancer, stomach cancer, head and neck cancer, kidney cancer, liver cancer, lung cancer, nasopharyngeal cancer, ovarian cancer, pancreas cancer, gallbladder carcinoma, prostate cancer, thyroid cancer, osteosarcoma, rhabdomyosarcoma, synovial sarcoma, Kaposi's sarcoma, leiomyosarcoma, malignant fibrous histicytoma, fibrosarcoma, adult T-cell leukemia, lymphoma, multiple myeloma, glioblastoma/astrocytoma, melanoma mesothelioma, and Wilms' tumor.

A sample may include any one of various biological samples as long as the target cell exists therein. For example, the biological sample may be selected from the group consisting of a biopsy sample, a tissue sample, a cell suspension in which a separated cell is suspended in a liquid medium, a cell culture, and a combination thereof. The biological sample may be selected from the group consisting of blood, bone marrow, saliva, lachrymal fluid, urine, semen, mucous fluid, and a combination thereof. For example, blood may be used as a sample to separate CTCs.

A ligand that is specific to a surface marker of a target cell may be bound to fine beads. The fine beads may be bound to the target cell to increase the density of the target cell. The fine beads may have a density that may cause a difference between the density of the target material in a sample and the density of the remaining cells other than the target cell. For example, when blood containing a cancer cell as a target cell is used as a biological sample, since densities of a white blood cell and a red blood cell are respectively about 1.07 $g/cm^3$ and about 1.1 $g/cm^3$, fine beads with an appropriate density may be selected in consideration of such densities. The fine beads may include beads, for example, selected from the group consisting of polystyrene particles, polymethylmetaacrylate particles, latex particles, acrylonitril-butadiene-styrene copolymer (ABS) particles, cyclic olefin copolymer particles, melamine particles, and a composite thereof, but may not be limited thereto. A diameter of the fine beads may vary according to a target cell to be separated and fine beads to be used, and may be, for example, in a range of about 1 nm to about 100 µm, or about 10 nm to about 10 µm. The fine beads may be nano beads or micro beads.

The surface marker may include a marker selected from the group consisting of a protein, sugar, lipid, a nucleic acid, and a combination thereof. For example, the surface marker may be a protein that is specifically expressed in cancer or tumor cells and is displayed on a cell membrane, and for example, may be EpCAM, c-Met, cytokeratines, CD45, Her2, or a combination thereof. In addition, the ligand that is specific to the surface marker may be an antibody that specifically connects to an antigen protein.

Hereinafter, a method of enriching a target cell using the microfluidic apparatus 1 of FIGS. 1B and 1C, according to a first embodiment, is described in detail. In the present embodiment, blood containing circulating cancer cells is used as a sample. The microfluidic apparatus 1 is able to contain a relatively large amount of blood, for example about 1 mL to about 20 mL. Such a large amount of biological sample may not be processed by conventional rotating microfluidic apparatus which are typically designed for applications in clinical chemistry or immunoassay with plasma and contain a relatively small amount of biological sample, such as few uL.

[Preparation]: Blood (for example, about 5 mL) containing circulating cancer cells as a target cell and fine beads (for example, about $1\times10^8$ or more) with an antibody that specifically connects to an antigen of the target cell are loaded into a sample chamber 110 through the inlet h1. In addition, appropriately selected DGM is loaded into the separation chamber 210 through the inlet h2. DGM may include, for example, Ficoll, Percoll, polysaccharide, NaCl solution, or the like. White blood cells and circulating cancer cells have similar physical properties, and accordingly, when they are centrifuged based on a density gradient, the white blood cells and circulating cancer cells are isolated in an identical layer. Accordingly, according to the present embodiment, fine beads are bound to circulating cancer cells to induce a density difference from white blood cells, thereby allowing the separation of only cancer cells from blood. Fine beads may be, for example, melamine particles, and a density thereof may be, for example, about 1.57 $g/cm^3$, which is greater than the density of biological particles in blood, that is, about 1.05 to 1.1 $g/cm^3$.

[Formation of target material (target cell-fine beads complex)]: The microfluidic apparatus 1 is mounted on the rotation driving unit 510, and then, the microfluidic apparatus 1 is rotated back and forth in clockwise and counterclockwise directions for a predetermined period of time so as to agitate and mix the fine beads with the target cells and hence bring fine beads in contact with target cells, thereby attaching the fine beads to the target cells. By doing so, a target material (e.g., target cell-fine beads comples)—is formed in the sample chamber 110.

[Transportation of fluid]: Using the electromagnetic wave generator 520, an electromagnetic wave, for example, a laser beam, irradiates the fluid supplying valve 15 to open the fluid supplying channel 10. For example, the valve material V1 melts, thereby opening the fluid supplying channel 10. When the microfluidic apparatus 1 is rotated (e.g., clockwise or counterclockwise), a fluid housed in the sample chamber 110 is transported to the separation chamber 210 housing DGM through the fluid supplying channel 10 due to a centrifugal force.

[Separation of target material based on a density gradient in the separation chamber 210]: The microfluidic apparatus 1 is rotated, e.g., for about 5 minutes for example, at 3000 rpm. As a result, a plurality of layers, which are distinguished from each other according to a density gradient of materials constituting a sample, are formed in the separation chamber 210. For example, a sample is divided into a DGM layer, a red blood cell layer, a white blood cell layer, and a plasma layer in the separation chamber 210. Due to the binding between target cells and fine beads, the density of the target material is the highest, and accordingly, the target cell may be separated in the form of the target material with the fine beads bound thereto from the white blood cell layer, and will typically be located in the lowest material layer of the separation chamber 210, that is, the farthest from the rotation center RC in the radial direction. The DGM layer, the red blood cell layer, the white blood cell layer, and the plasma layer are located in the upper material layers, sequentially closer to the rotation center RC.

Figure 8A:
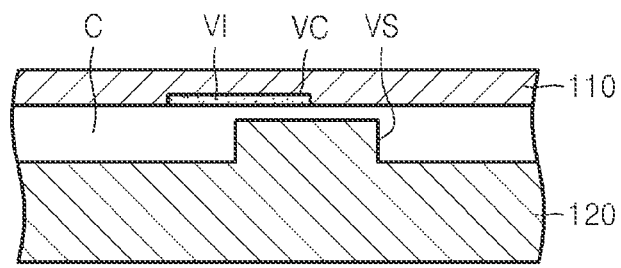
FIGS. 8A, 8B and 8C are cross-sectional views of an open/close valve according to an embodiment.
Figure 8B:
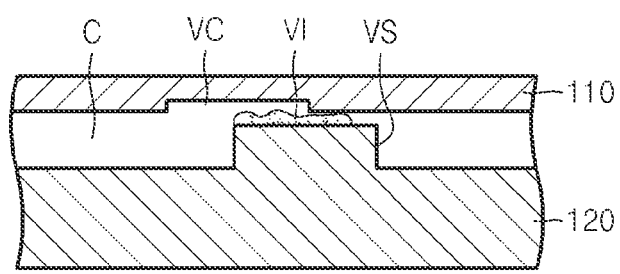

[Recovering of the target material]: The microfluidic apparatus 1 is stopped from rotating, and then, the target material is extracted from the separation chamber 210 through an extraction hole (not shown) by using, for example, a pipette. To increase the reliability of recovering a target material, an additional automatic process may be used. To do this, using the electromagnetic wave generator 520, an electromagnetic wave, for example, a laser beam, irradiates the recovering valve 25 to open the recovery channel 20. When the microfluidic apparatus 1 is rotated, the target material located in the lowest layer of the separation chamber 210 is transported to the recovery chamber 220 through the recovery channel 20 due to the centrifugal force. In this regard, the recovery valve 25 may be a valve that is opened or closed as illustrated in FIGS. 8A and 8B, respectively. When the target material is completely transported, the microfluidic apparatus 1 is stopped from rotating and a laser beam irradiates the recovery valve 25 to close the recovery channel 20.

When the microfluidic apparatus 1 of FIG. 1C is used, a fluid located above the target material layer may be first discharged to reduce the in-flow of foreign materials and to improve an enrichment rate. For example, using the electromagnetic wave generator 520, an electromagnetic wave, for example, a laser beam, irradiates the discharge valve 35. Due to the irradiation, the valve material V1 may melt, and thus, the discharge channel 30 opens. When the microfluidic apparatus 1 is rotated, the remaining fluid other than the target material housed in the separation chamber 210 is transported to the waste chamber 300 through the discharge channel 30 due to a centrifugal force. The microfluidic apparatus 1 is stopped from rotating, using the electromagnetic wave generator 520, an electromagnetic wave, for example, a laser beam, irradiates the recovery valve 25 to open the recovering channel 20. Then, when the microfluidic apparatus 1 is rotated, the target material flows into the recovery chamber 220 through the recovery channel 20 due to a centrifugal force.

The target material may be extracted through an extraction hole (not shown) provided in the recovery chamber 220. By doing so, a target cell in blood may be enriched by the separation from the blood.

The density and size of the target material may increase compared to those of other cells in blood, and thus, the target material may be easily separated by filtering. Accordingly, post filtering may enable the separation of an enriched target material from the fluid.

FIG. 3 is a plan view of the microfluidic apparatus 1 according to an embodiment. The microfluidic apparatus 1 according to the present embodiment is different from the microfluidic apparatus 1 illustrated in FIG. 1B in that a sample and fine beads are separately housed. Referring to FIG. 3, the sample supplying unit 100 includes a sample chamber 110 and a particle chamber 120. The sample chamber 110 houses a sample. The sample chamber 110 may include a partition wall 400 to partially restrict the flow of a fluid in the radial direction, which will be described in connection with FIGS. 11 to 14. The particle chamber 120 houses fine beads. The particle chamber 120 should be located closer to the rotation center RC in the radial direction than the sample chamber 110. The particle chamber 120 is connected to the sample chamber 110 through a first channel 40, which includes a first valve 45 to control the flow of a fluid through channel 40. The first valve 45 is a closed value illustrated in FIGS. 2A and 2B, and can be selectively activated, e.g., using electromagnetic energy, to open the first channel 40. The fine beads may be housed together with a convey fluid, that is, a buffer in the particle chamber 120 to enable the fine beads to be easily supplied to the sample chamber 110 through the first channel 40. The particle chamber 120 may be connected to the sample chamber 110 proximal to each of the first and second regions 101 and 102.

Hereinafter, a method of enriching a target cell by using the microfluidic apparatus 1 illustrated in FIG. 3, according to a second embodiment, will be described. In the present embodiment, blood containing circulating cancer cells is used as a sample.

[Preparation]: Blood containing a circulating cancer cell as a target cell is loaded into the sample chamber 110 through the inlet h1. In addition, appropriately selected DGM is loaded into the separation chamber 210 through the inlet h2. In addition, fine beads with an antibody that specifically connects to an antigen of the target cell is loaded together with a buffer into the particle chamber 120 through an inlet h3.

[Transportation of fine beads]: The microfluidic apparatus 1 is mounted on the rotation driving unit 510, and using the electromagnetic wave generator 520, an electromagnetic wave, for example, a laser beam, irradiates the first valve 45 to open the first channel 40. The microfluidic apparatus 1 is rotated to transport the fine beads together with the buffer from the particle chamber 120 to the particle chamber 120 due to a centrifugal force.

Then, [transportation of fluid], [separation of target material based on density gradient in the separation chamber 210], and [recovering of target material] are performed to enrich the target cell by separation from blood. In addition, filtering is typically performed as a post process to obtain an enriched target material separated from the fluid.

The specific binding of fine beads and a target cell may depend on an antigen-antibody binding described above. A sample may contain various kinds of proteins and such proteins may prohibit the specific bond between the fine beads and the target cell. For example, binding between the fine beads and the target cell may be prevented when a protein that has a structure similar to that of an antigen is bound to a surface marker of a target cell in advance. In addition, binding between the fine beads and the target cell may be prevented when a protein that has a structure similar to that of an antibody is bound to a ligand of the fine beads. As such, proteins in a sample prevent the generation of a target cell-fine beads complex, thereby lowering the enrichment efficiency of the target cell. To prevent the decrease in enrichment efficiency, proteins in the sample may be removed from the sample before the fine beads are mixed with the sample.

Figure 4:
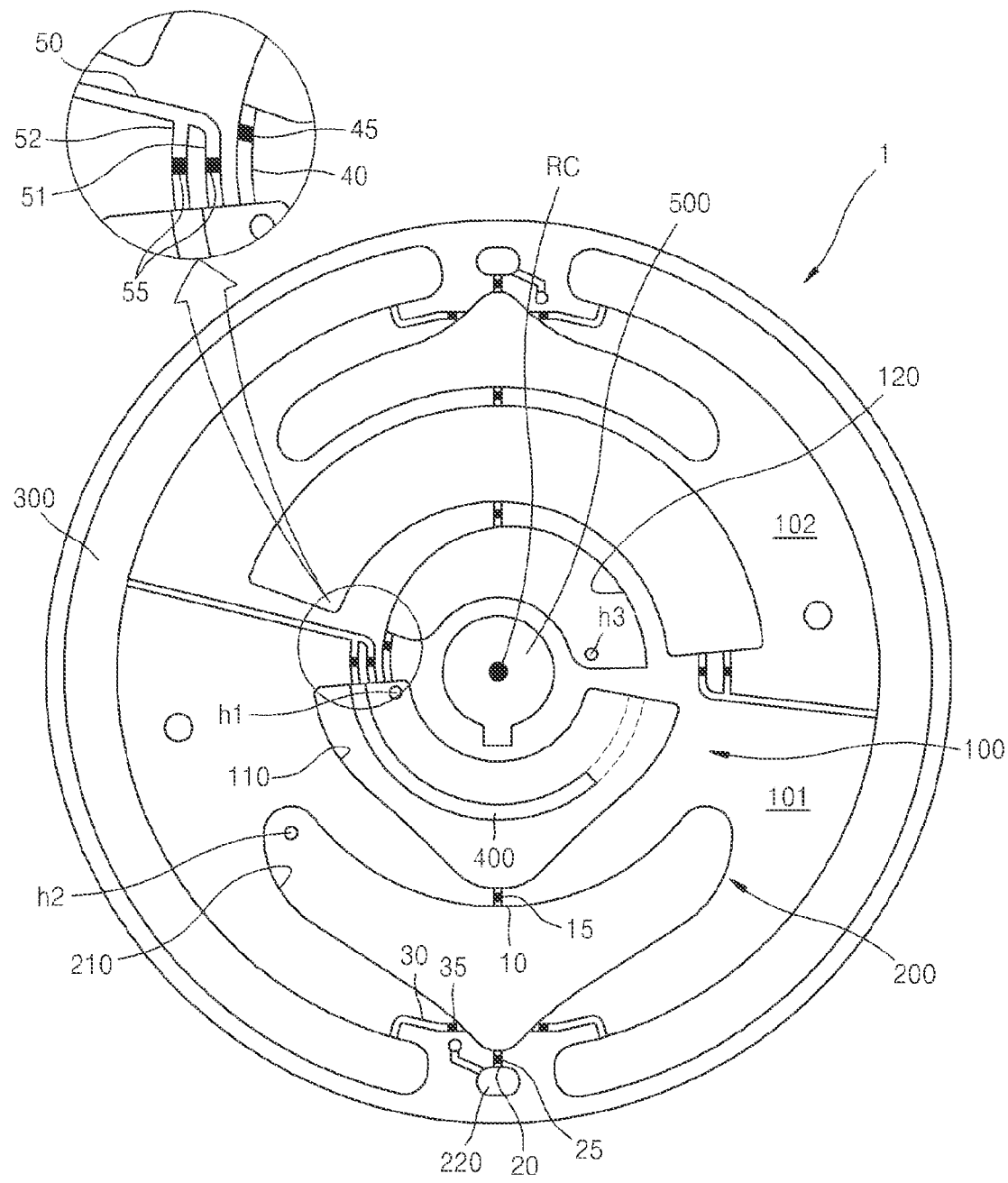
FIG. 4 is a plan view of a microfluidic apparatus including a waste chamber, according to an embodiment.

FIG. 4 is a plan view of the microfluidic apparatus 1 according to an embodiment. The microfluidic apparatus 1 according to the present embodiment is different from the microfluidic apparatus 1 illustrated in FIG. 3, in that after the sample housed in the sample chamber 110 is centrifuged, an upper material layer located above a target layer containing a target cell is removed. The sample chamber 110 may include a partition wall 400 to partially restrict the flow of a fluid in the radial direction, which will be described in connection with FIGS. 11 to 14. FIG. 4 illustrates a waste chamber 300, which is connected to the sample chamber 110 by the second channel 50. The waste chamber 300 is disposed outside the sample chamber 100 in the radial direction from the rotation center RC. In the present embodiment, the waste chamber 300 is connected to the separation chamber 210 and the sample chamber 110. However, according to another embodiment, the separation chamber 210 and the sample chamber 110 may be connected to two different waste chambers. A connection location of the second channel 50 and the sample chamber 110 may vary according to an amount of the upper material layer of the sample. For example, when blood is used as a sample, plasma may be removed from the blood. In this regard, a composition ratio of blood may vary according to the patient, and thus, an amount of plasma may also vary. The second channel 50 according to the present embodiment may include two connection channels 51 and 52. The connection channels 51 and 52 may be connected to the sample chamber 110 at different locations in the radial direction from the rotation center RC. The connection channels 51 and 52 each include a second valve 55. The second valve 55 may be a normally closed valve illustrated in FIGS. 2A and 2B and may receive electromagnetic energy to open the connection channels 51 and 52. According to an amount of the upper material layer to be removed, one of the connection channels 51 and 52 may be opened. When an amount of the upper material layer is relatively small, the connection channel 51, which is closer to the rotation center RC than the connection channel 52, is opened, and when an amount of the upper material layer is relatively great, the connection channel 52, which is farther from the rotation center RC than the connection channel 51, is opened. The number of connection channels may be three or more.

Hereinafter, a method of enriching a target cell by using the microfluidic apparatus 1 illustrated in FIG. 4, according to a third embodiment, will be described. In the present embodiment, blood containing circulating cancer cells is used as a sample.

[Preparation]: Blood containing a circulating cancer cell as a target cell is loaded into the sample chamber 110. In addition, fine beads with an antibody that specifically connects to an antigen of the target cell is loaded together with a buffer into the particle chamber 120. In addition, appropriately selected DGM is loaded into the separation chamber 210. DGM may be loaded into the separation chamber 210 in advance as described above. Since the first channel 40 is closed by the first valve 45, fine beads are separated from the sample.

[Centrifuging of a sample]: The microfluidic apparatus 1 is mounted on the rotation driving unit 510, and then, rotated at a rotation rate of about 1000 to about 8000 rpm, for example, at about 3000 rpm for about 5 minutes. By doing so, the blood in the sample chamber 110 will be divided into a plurality of layers based on a density difference between the materials making up those layers. A red blood cell layer containing the heaviest red blood cell is located farthest away in the radial direction from the rotation center RC. Then, a target layer including a white blood cell and a target cell, and a plasma layer, which is an upper material layer, are sequentially located closer to the rotation center RC. Since proteins in blood are lighter than blood corpuscles, the proteins are located in the plasma layer.

[Discharge of plasma]: The microfluidic apparatus 1 is stopped from rotating, and using the electromagnetic wave generator 520, an electromagnetic wave, for example, a laser beam, irradiates the second valve 55 of one of the connection channels 51 and 52 which is determined according to an amount of plasma to open the second channel 50. During the discharge of plasma, blood cells should not be discharged to the waste chamber 300. Which of the connection channels 51 and 52 is opened may be determined based on the initial volume of the sample in the sample chamber 110, for example. Alternatively, after the centrifugation of the sample, absorbance of the sample may be measured. Based on the measurement, a position of the plasma layer in the sample chamber 110 may be determined and one of the connection channels 51 and 52 may be opened to discharge the plasma to the waste chamber 300. Then, the microfluidic apparatus 1 is rotated again, and the plasma is discharged to the waste chamber 300 through the second channel 50 due to a centrifugal force. In this process, all or at least a portion of blood proteins, which prevent the binding between a target cell and fine beads, may be discharged together with the plasma to the waste chamber 300.

[Transportation of fine beads]: When the discharge of plasma is completed, the microfluidic apparatus 1 is stopped from rotating, and using the electromagnetic wave generator 520, an electromagnetic wave, for example, a laser beam, irradiates the first valve 45 to open the first channel 40. The microfluidic apparatus 1 is then rotated again, and the fine beads are conveyed together with a buffer from the particle chamber 120 to the sample chamber 110 due to the centrifugal force.

[Formation of target material (target cell-fine beads complex)]: The microfluidic apparatus 1 is rotated back and forth in clockwise and counterclockwise directions for a predetermined period of time to bring the fine beads in contact with target cells, thereby attaching the fine beads to the target cells. By doing so, a target cell-fine beads complex, that is, a target material, is formed in the sample chamber 110. Since blood proteins are discharged together with plasma to the waste chamber 300, the binding efficiency between the fine beads and the target cells is improved.

Then, [transportation of fluid], [separation of target material based on density gradient in the separation chamber 210], and [recovering of target material] according to the first embodiment are performed to enrich the target cell by separation from blood. In addition, filtering is performed as a post process to obtain an enriched target material which is separated from the fluid.

Figure 5:
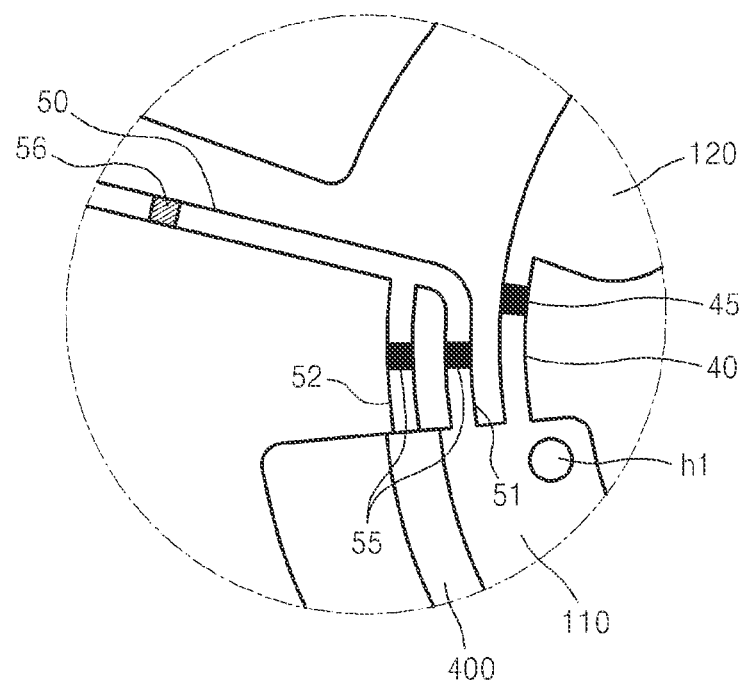
FIG. 5 shows a diagram of a second channel with a normally open valve.

After the fine beads are conveyed together with a buffer to the sample chamber 110, the microfluidic apparatus 1 is rotated in a clockwise/counter-clockwise direction to mix the fine beads with a sample. In this regard, a level of the fluid in the sample chamber 110 elevates to a degree where the target cell spills to the waste chamber 300 together with the fluid through the open second channel 50. To prevent such a leakage, as illustrated in FIG. 5, the second channel 50 may further include a third valve 56, which can be selectively activated, e.g., closed, to prevent fluid flow. The third valve 56 may be disposed closer to the waste chamber 300 than the second valve 55. The third valve 56 is a normally open valve, and only when the third valve 56 receives energy, the third valve 56 closes a channel, and before this, the third valve 56 opens the channel to allow the fluid to flow.

Figure 6A:
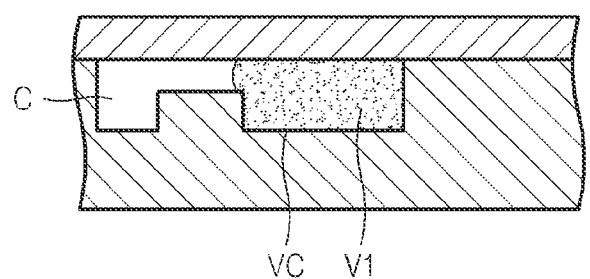
FIGS. 6A and 6B are cross-sectional views of a normally open valve according to an embodiment.
Figure 6B:
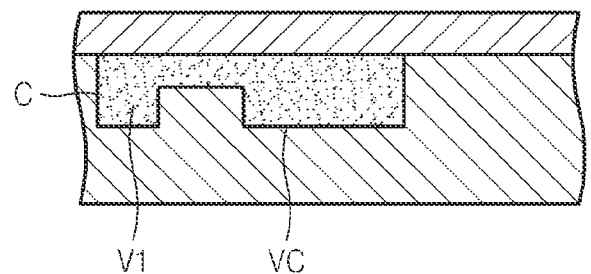

FIGS. 6A and 6B are cross-sectional views of an example of a normally open valve and the valve in a closed state, respectively. The normally open valve includes a channel C, a valve chamber VC extending from the channel C in a width direction of the channel C, and a valve material V1 filling the valve chamber VC. As illustrated in FIG. 6A, before external energy is supplied to the valve material V1, the channel C is maintained open because the valve material V1 exists in the valve chamber VC. However, when external energy is supplied to the valve material V1, the valve material V1 melts and expands, thereby flowing into the channel C and solidifying therein, thereby blocking the flow of the fluid through the channel C.

Hereinafter, a method of enriching a target cell by using the microfluidic apparatus 1 illustrated in FIG. 5, according to a fourth embodiment, will be described. In the present embodiment, blood containing circulating cancer cells is used as a sample.

[Preparation], [centrifugation of sample], and [discharge of plasma] of the method of enriching a target cell according to the third embodiment are performed.

[Closing of Second Channel 50]

Using the electromagnetic wave generator 520, an electromagnetic wave, for example, a laser beam, irradiates the third valve 56. Due to the irradiation, as illustrated in FIG. 6B, the valve material V1 melts and solidifies, thereby closing the second channel 50.

Thereafter, [transportation of fine beads], [formation of target material (target cell-fine beads complex)], [transportation of fluid], [separation of target material in the separation chamber 210 based on density gradient], and [target material recovering] according to the third embodiment are performed to enrich the target cell by separation from blood.

In addition, filtering is performed as a post process to obtain an enriched target material separated from the fluid. Since the second channel 50 is closed, when the process of [formation of target material (target cell-fine beads complex)] is performed, the leakage of the fluid containing a target cell from the sample chamber 110 to the waste chamber 300 through the second channel 50 may be prevented.

As described above, due to the buffer conveyed to the sample chamber 110 together with the fine beads, the level of the fluid in the sample chamber 110 increases. To increase a contact possibility between the fine beads and the target cell in the process of [formation of target material (target cell-fine beads complex)], it is better that the amount of the fluid in the sample chamber 110 be smaller. Accordingly, the buffer supplied to the sample chamber 110 together with fine beads may be removed. The buffer is present in the upper material layer when centrifuging is performed in the sample chamber 110. Thus, after the separation of plasma, a second centrifugation may be further performed to discharge the buffer to the waste chamber 300 through the second channel 50. During removal of the plasma, the second channel 50 is in an open state. Accordingly, during the second centrifugation, the second channel 50 is maintained in a closed state, and after the second centrifugation, the second channel 50 is opened to discharge the buffer to the waste chamber 300 through the second channel 50.

Figure 7:
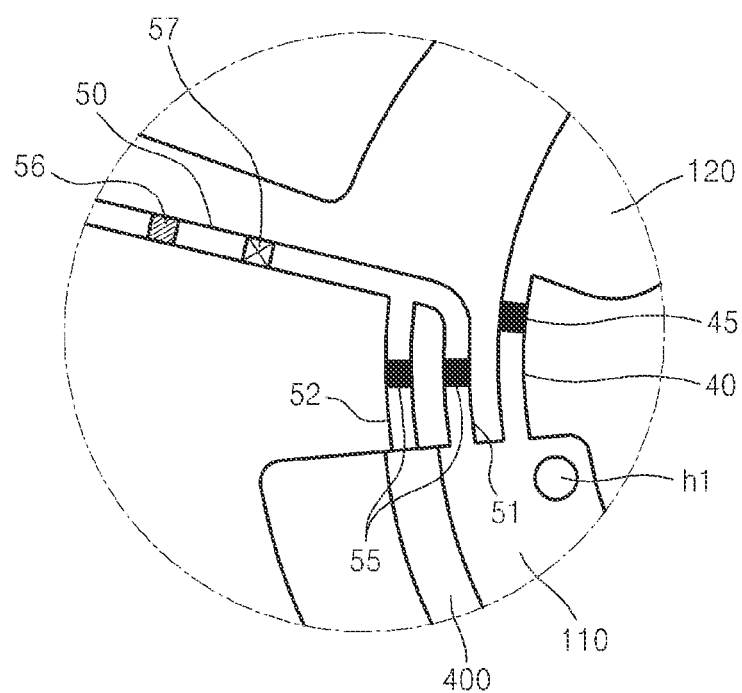
FIG. 7 shows a diagram of a second channel with an open/close valve.

To do this, as illustrated in FIG. 7, the second channel 50 may further include a fourth valve 57. The fourth valve 57 is an open/close valve, that is, a valve that can be sequentially converted into open state/closed state/re-opened state. Although the fourth valve 57 illustrated in FIG. 7 is located farther from the waste chamber 300 than the third valve 56, the third valve 56 may instead be located farther from the waste chamber 300 than the fourth valve 57.

Figure 8C:
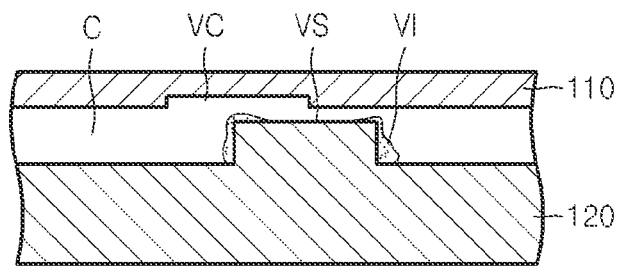

FIGS. 8A to 8C are cross-sectional views of an example of an open/close valve 57. Referring to FIG. 8A, the open/close valve includes a channel C, a valve chamber VC located at a higher level than the channel C, a valve material V1 filling the valve chamber VC, and a step VS that partially overlaps with and protrudes toward the valve chamber VC under the valve chamber VC in the channel C. As illustrated in FIG. 8A, before external energy is supplied to the valve material V1, the channel C is maintained open because the valve material V1 exists in the valve chamber VC. When external energy is supplied to the valve material V1, the valve material V1 melts and expands, thereby flowing onto the step VS, and then, the valve material V1 is solidified, thereby blocking the flow of the fluid through the channel C as illustrated in FIG. 8B. When a stronger external energy is supplied to the solidified valve material V1, the valve material V1 located on the step VS melts and becomes fluid. Thus, the valve material V1 flows into the channel C over the step VS. As a result, as illustrated in FIG. 8C, the channel C is re-opened. Referring to FIGS. 8A and 8B, the valve operates as a normally open valve. Therefore, instead of the normally open valve illustrated in FIGS. 6A and 6B, the valve illustrated in FIGS. 8A and 8B may be used. Also, seeing FIGS. 8B and 8C, the valve operates as a normally closed valve. Therefore, instead of the normally closed valve illustrated in FIGS. 2A and 2B, the valve illustrated in FIGS. 8B and 8C may be used.

Hereinafter, a method of enriching a target cell by using the microfluidic apparatus 1 illustrated in FIG. 7, according to a fifth embodiment, will be described. In the present embodiment, blood containing circulating cancer cells is used as a sample.

[Preparation], [centrifugation of sample], and [discharge of plasma] of the method of enriching a target cell according to the third embodiment are performed.

[Removing of Buffer]

After plasma is discharged, using the electromagnetic wave generator 520, an electromagnetic wave, for example, a laser beam, irradiates the fourth valve 57 to close the second channel 50 as illustrated in FIG. 8B. In this state, the microfluidic apparatus 1 is rotated to perform centrifugation. Due to the centrifugation, the buffer with the lowest density forms an upper material layer. Then, the electromagnetic wave generator 520 is used to irradiate the fourth valve 57 using an electromagnetic wave, for example, a laser beam, to open the second channel 50 as illustrated in FIG. 8C. Then, the microfluidic apparatus 1 is rotated and due to the centrifugal force, the buffer included in the sample chamber 110 is discharged to the waste chamber 300 through the second channel 50.

Then, as described according to the fourth embodiment of the target cell enrichment method, [closing of the second channel 50] is performed. Thereafter, [formation of target material (target cell-fine beads complex)], [transportation of fluid], [separation of target material in the separation chamber 210 based on density gradient], and [target material recovering] according to the third embodiment are performed to enrich the target cell by separation from blood. In addition, filtering is performed as a post process to obtain an enriched target material separated from the fluid.

When a relatively large cell is included in a sample, the contact possibility between fine beads and a target cell may decrease during the formation of a target cell-fine beads complex. Accordingly, a lysis solution that dissolves a particular cell in a sample is added thereto to remove a relatively large cell, thereby improving the contact possibility between the fine beads and the target cell. For example, in the case of blood, a red blood cell has the largest size from among cells constituting blood. To increase the contact possibility between the fine beads and the target cell in the sample chamber 110, the red blood cell in blood may be removed. For example, a red blood cell (RBC) lysis solution that dissolves RBC is added into the sample chamber 110. When exposed to the RBC lysis solution for a long period of time, white blood cells and cancer cells may lose their activities. However, since RBC does not have a plasma membrane, RBC dissolves relatively quickly. For example, when exposed to the RBC lysis solution for about 10 minutes, the RBC dissolves and white blood cells and cancer cells do not dissolve.

Figure 9:
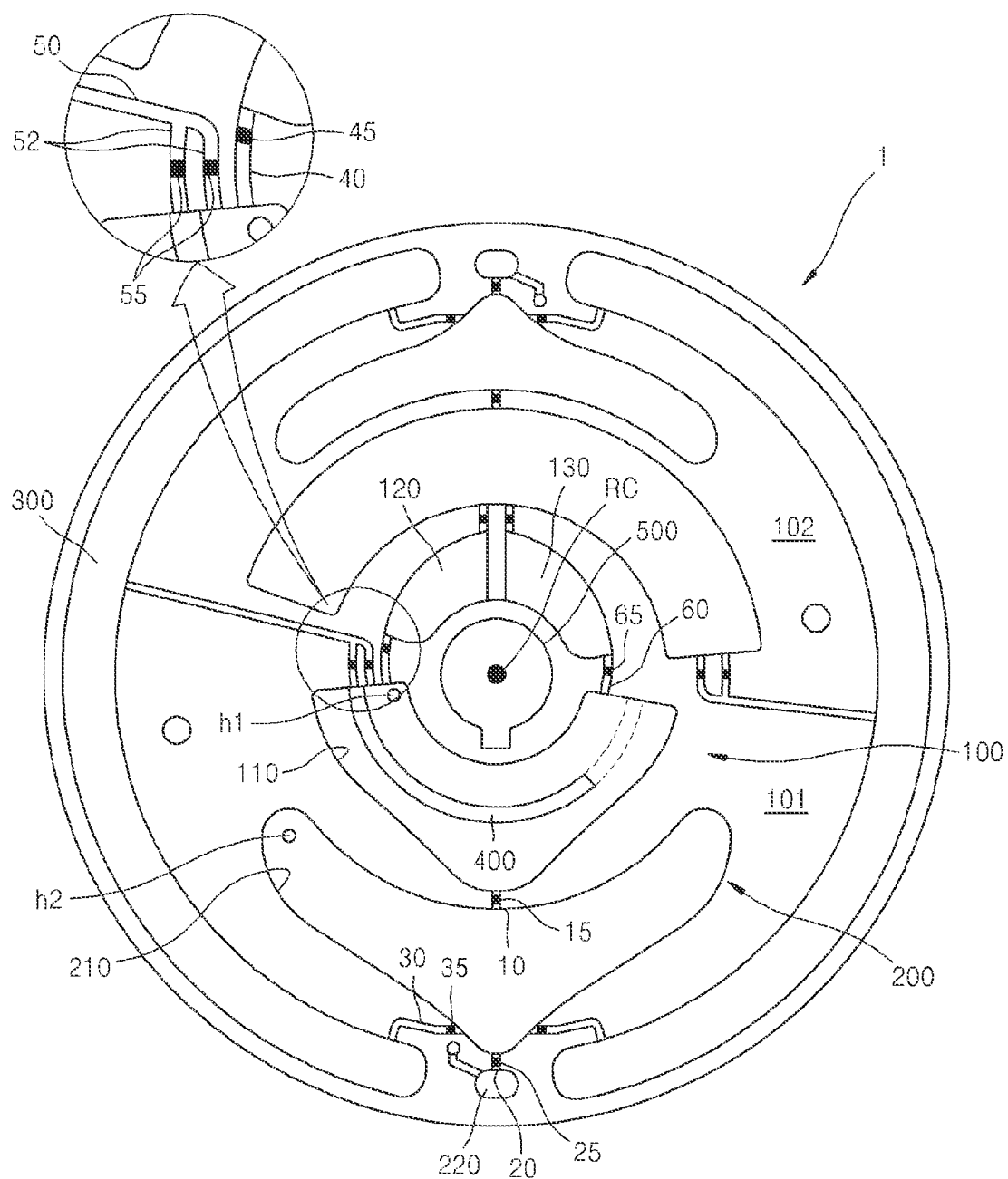
FIG. 9 is a plan view of a microfluidic apparatus including a lysis solution chamber, according to an embodiment.

FIG. 9 is a plan view of the microfluidic apparatus 1 according to an embodiment. Referring to FIG. 9, a lysis solution chamber 130 is further provided to the microfluidic apparatus 1. The lysis solution chamber 130 may be located closer to the rotation center RC than the sample chamber 110 in the radial direction to allow a lysis solution to be supplied the sample chamber 110 due to a centrifugal force. The lysis solution chamber 130 is connected to the sample chamber 110 by the third channel 60. The third channel 60 may include a fifth valve 65 to control the flow of fluid therethrough. The fifth valve 65 is a normally closed valve as illustrated in FIGS. 2A and 2B. Although FIG. 9 illustrates only the second valve 55 provided to the second channel 50, as illustrated in FIGS. 5 and 7, the third valve 56 and the fourth valve 57 may also be provided. The sample chamber 110 may include a partition wall 400 to partially restrict the flow of a fluid in the radial direction, which will be described in connection with FIGS. 11 to 14.

Hereinafter, a method of enriching a target cell by using the microfluidic apparatus 1 illustrated in FIG. 9, according to a sixth embodiment, will be described.

[Preparation]: The second to fifth embodiments of the target cell enrichment method may be applied to the sixth embodiment of the target cell enrichment method. In addition to [Preparation] of the second embodiment of the target cell enrichment method, a lysis solution may be loaded into the lysis solution chamber 130, e.g., using a port (not shown).

[Transportation of lysis solution]: The microfluidic apparatus 1 is mounted on the rotation driving unit 510, and using the electromagnetic wave generator 520, an electromagnetic wave, for example, a laser beam, irradiates the fifth valve 65 to open the third channel 60. Then, the microfluidic apparatus 1 is rotated to load the lysis solution into the sample chamber 110 due to the centrifugal force. When loading of the lysis solution is completed, the microfluidic apparatus 1 is rotated in a clockwise/counter-clockwise direction to mix the sample and the lysis solution, and then the resultant mixture was maintained for a predetermined period of time to dissolve a macro cell in the sample, for example, a RBC in blood.

After the process of [Transportation of lysis solution] is performed, as described in the second to fifth embodiments of the target cell enrichment method, [centrifugation of sample], [discharge of plasma], [transportation of fine beads], [removing of buffer], [closing of second channel], [formation of target material (target cell-fine beads complex)], [transportation of fluid], [separation of target material based on density gradient in separation chamber 210], and [target material recovering] are performed to enrich the target cell by separation from blood. In addition, filtering is performed as a post process to obtain an enriched target material separated from the fluid.

In the previous embodiments, the separation chamber 210 is disposed outside the sample chamber 110, and all or nearly all fluid in the sample chamber 110 is supplied to the separation chamber 210. However, embodiments are not limited thereto. For example, a first DGM with a higher density than the target cell may be added to the sample chamber 110, so that a target layer containing a target cell, or the target layer and an upper material layer are located on the first DGM, and the target layer is extracted from the sample chamber 110. The first DGM may include, for example, ficoll, percoll, or the like. Then, fine beads are added to the extracted fluid to form a target cell-fine beads complex, that is, a target material, and the fluid including the target material is transported to the separation chamber 210 to separate the target material based on a density difference.

Figure 10:
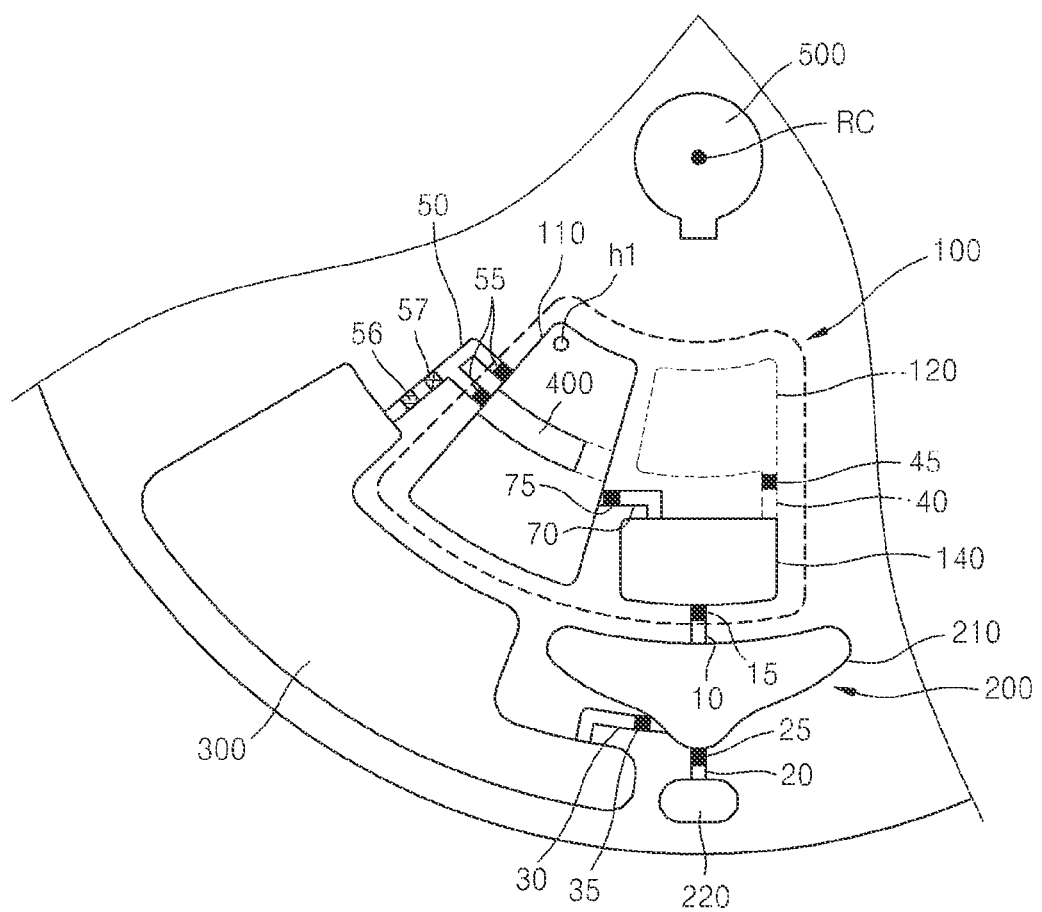
FIG. 10 is a plan view of a microfluidic apparatus including a reaction chamber, according to an embodiment.

FIG. 10 is a view of a microfluidic apparatus according to an embodiment. According to the present embodiment, only a portion of the fluid including the target material in the sample chamber 110 is provided to the separation chamber 210. Referring to FIG. 10, the sample supplying unit 100 includes the sample chamber 110 and a reaction chamber 140. The sample chamber 110 houses the first DGM and a sample. The sample chamber 110 of the microfluidic apparatus 1 may already house the first DGM in the manufacturing procedure of the microfluidic apparatus 1. In addition, the first DGM may be loaded into the sample chamber 110 through the inlet h1 to enrich a target cell. The sample may be loaded into the sample chamber 110 through the inlet h1. The first DGM has a higher density than the target cell included in the sample. Accordingly, during centrifugation, the fluid containing the target cell is located above the first DGM, that is, is located closer to the rotation center RC than the first DGM. For example, when the sample is blood, the first DGM may be a material that has smaller density than RBC and higher density than the target cell. By doing so, a target layer including the target cell and white blood cells and a plasma layer may be located above the first DGM. The sample chamber 110 may include a partition wall 400 to partially restrict the flow of a fluid in the radial direction, which will be described in connection with FIGS. 11 to 14.

In the reaction chamber 140, the target cell is combined with fine beads to form a target cell-fine beads complex, that is, a target material. The reaction chamber 140 is connected to the sample chamber 110 through the transport channel 70. The transport channel 70 is connected to the sample chamber 110 in such a way that the transport channel 70 is located adjacent to a top surface of the first DGM layer. For example, a connection location of the transport channel 70 to the sample chamber 110 may be determined based on an initial volume of the first DGM and an initial volume of the sample in the sample chamber 110. A transportation valve 75 is provided in the transport channel 70 to control the flow of fluid therethrough. The transportation valve 75 is a normally closed valve as illustrated in FIGS. 2A and 2B. The reaction chamber 140 may house fine beads. In addition, as indicated in a dotted line of FIG. 10, the fine beads may be housed in the particle chamber 120 that is connected to the reaction chamber 140 by the first channel 40 provided with the first valve 45.

The structure of the density-gradient separation unit 200 can be substantially the same as, or identical to, the structure illustrated in FIGS. 1B, 3, 4, and 9. The DGM housed in the separation chamber 210 may be identical to or different from the first DGM. For example, when the density of the first DGM is smaller than that of the target material, the first DGM and the DGM may be identical to each other.

The waste chamber 300 may house a portion of the upper material layer discharged from the sample chamber 110, for example, in the case of blood, plasma. In addition, the waste chamber 300 may house a fluid including the DGM discharged from the reaction chamber 140.

Hereinafter, a method of enriching a target cell by using the microfluidic apparatus 1 illustrated in FIG. 10, according to a seventh embodiment, will be described. In the present embodiment, blood containing circulating cancer cells is used as a sample.

[Preparation]: Blood containing a circulating cancer cell as a target cell and the first DGM are loaded into the sample chamber 110. In addition, fine beads with an antibody that specifically connects to an antigen of the target cell is loaded together with a buffer into the particle chamber 120 or the reaction chamber 140. In addition, appropriately selected DGM is loaded into the separation chamber 210.

[Centrifugation of sample]: The microfluidic apparatus 1 is mounted on the rotation driving unit 510, and then, rotated at a rotation rate of about 2,300 rpm for about 8 minutes. As a result, a RBC layer including the heavist RBC is located to the most outside in the radial direction due to a density difference in blood in the sample chamber 110. Then, the first DGM layer, the target layer including a white blood cell and a target cell, and an upper material layer including a plasma layer are sequentially located closer to the rotation center RC.

If needed, the processes of [discharging of plasma] and [removing of buffer] may be performed.

[Transportation of target cells]: Using the electromagnetic wave generator 520, an electromagnetic wave, for example, a laser beam, irradiates the transportation valve 75 to open the transport channel 70. Then, the microfluidic apparatus 1 is rotated to transport the fluid including a target cell located above the first DGM layer to the reaction chamber 140 due to a centrifugal force.

When the fine beads are housed in the particle chamber 120, the process of [transportation of fine beads] may be performed.

[Formation of target material (target cell-fine beads complex)]: The microfluidic apparatus 1 is rotated back and forth in clockwise and counterclockwise directions for a predetermined period of time to bring fine beads in contact with target cells, thereby attaching the fine beads to the target cells. By doing so, a target cell-fine beads complex, that is, a target material, is formed in the reaction chamber 140.

Then, [transportation of fluid], [separation of target material based on density gradient in the separation chamber 210], and [recovering of target material] are performed to enrich the target cell by separation from blood. In addition, filtering is performed as a post process to obtain an enriched target material separated from the fluid.

Regarding the microfluidic apparatus 1, to transport the target layer or to discharge the upper material layer disposed above the target layer to the waste chamber 300 after a sample housed in the sample chamber 110 is divided by centrifugation into a plurality of layers based on a density gradient, the microfluidic apparatus 1 is stopped from rotating and then a valve is opened. Since the microfluidic apparatus 1 is not rotated at this time during the process, a centrifugal force is not applied to the sample housed in the sample chamber 110, and after some time elapses, a plurality of layers may be slowly mixed together due to molecular motions in the sample. In this case, the target cell may be mixed with an upper material layer, which decreases the enrichment efficiency of the cell, or the target cell may be mixed with an upper material layer to be discharged to the waste chamber 300. Such disadvantages may be caused when the buffer is removed. In addition, when the target layer including a target cell is transported to the reaction chamber 140 of the microfluidic apparatus 1 illustrated in FIG. 10, the stopping of the microfluidic apparatus 1 and the opening of the transportation valve 75 are needed, and in this process, the target layer in the sample chamber 110 may be mixed with other layers, and thus, a smaller amount of the target cell may be transported to the reaction chamber 140. Thus, a material that is not necessary for the target layer in the sample may be mixed with the target layer.

Referring to FIGS. 1B, 3, 4, 9, and 10, the sample chamber 110 includes the partition wall 400 to prevent a plurality of layers from mixing due to gravity after centrifugation. A detailed structure of the partition wall 400 is described in connection with FIG. 11.

Figure 11:
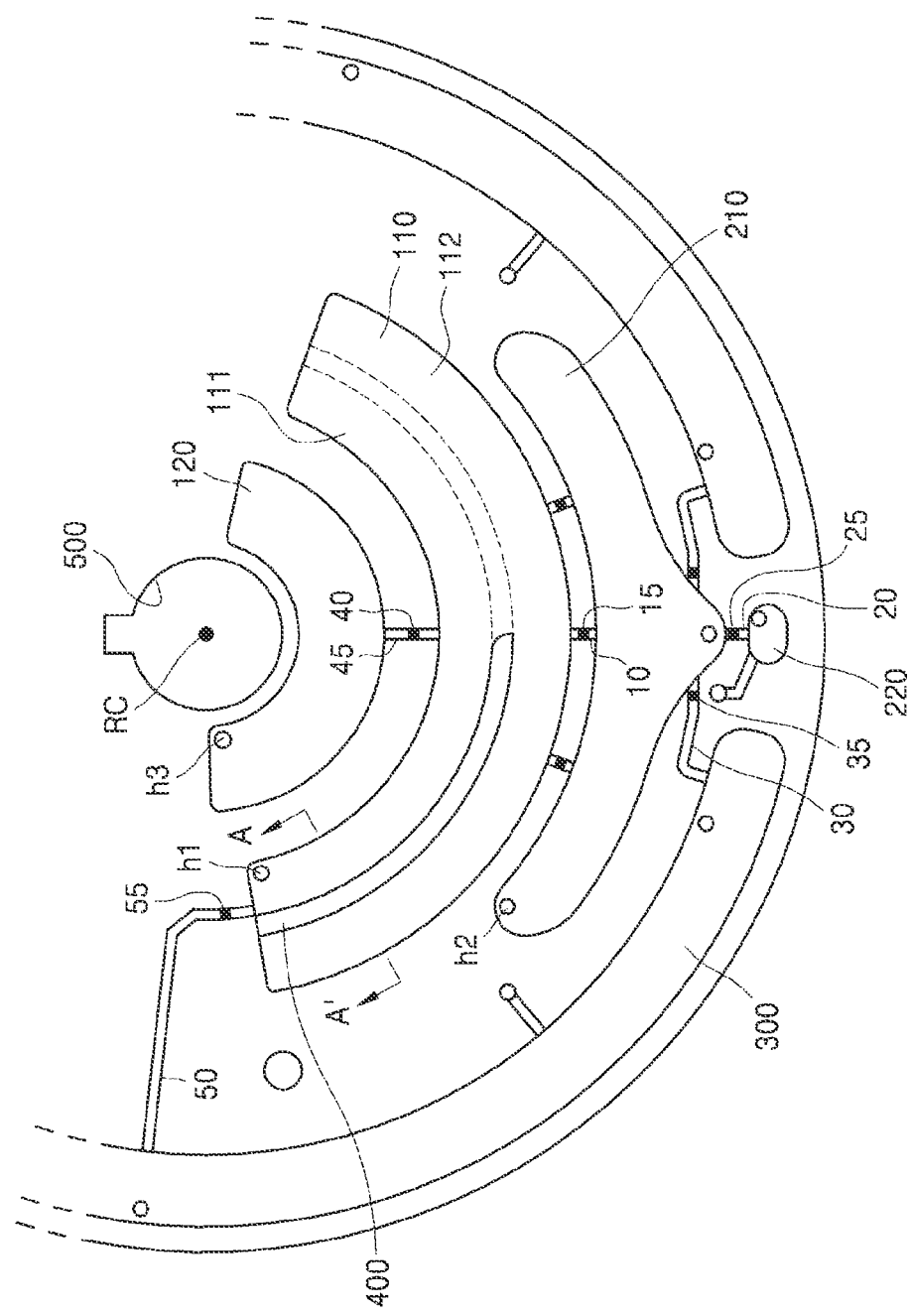
FIG. 11 is a plan view of a microfluidic apparatus including a partition wall disposed in a sample chamber, according to an embodiment.
Figure 12:
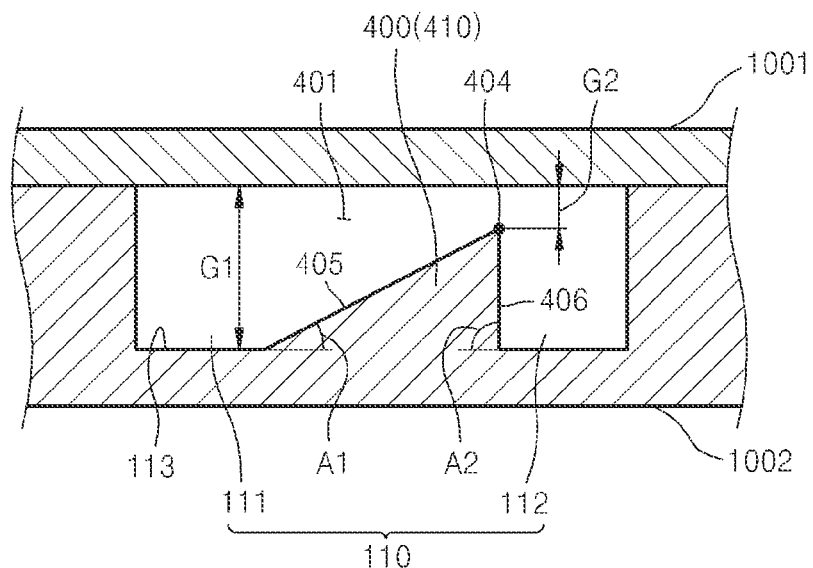
FIG. 12 is a cross-section taken along line A-A' of FIG. 11.

FIG. 11 is a plan view of the microfluidic apparatus 1 according to an embodiment. FIG. 12 is a cross-section taken along line A-A' of FIG. 11. In the microfluidic apparatus 1, the movement of a fluid in the sample chamber 110 in the radial direction is partially restricted due to the presence of partition wall 400. That is, referring to FIGS. 11 and 12, the sample chamber 110 includes the partition wall 400 to partially restrict the flow of the sample in the radial direction. For example, the partition wall 400, as illustrated in FIG. 12, may extend from a bottom wall 1002 of the sample chamber 110 up toward a top wall 1001 of the sample chamber 110. As illustrated in FIG. 11, the partition wall 400 may occupy a portion of the width of the sample chamber 110 in the circumference direction of the sample chamber 110. However, as indicated in a dotted line of FIG. 11, the partition wall 400 may occupy the entire width of the sample chamber 110 in the circumference direction of the sample chamber. Due to the partition wall 400, the sample chamber 110 is divided into an inner region 111, which is relatively close to the rotation center RC in the radial direction, and an outer region 112, which is relatively far from the rotation center RC in the radial direction. The partition wall 400 and the top wall 1001 may form a bottleneck portion 401 therebetween. The bottleneck portion 401 may connect the inner region 111 to the outer region 112. Although not illustrated in FIG. 11, the partition wall 400 may extend from the top wall 1001 of the sample chamber 110 toward the bottom wall 1002 of the sample chamber 110 to form the bottleneck portion 401 between the top wall 1001 and the bottom wall 1002.

During centrifugation of a sample, due to the centrifugal force, the sample flows from the inner region 111 to the outer region 112 across the bottleneck portion 401 to form a plurality of layers based on a density gradient in the sample chamber 110. When the microfluidic apparatus 1 is stopped from rotating, and thus, the centrifugal force disappears, the bottleneck portion 401 may restrict the movement of the sample between the inner region 111 and the outer region 112. That is, the flow of a fluid in the radial direction in the sample chamber 110 is restricted by the partition wall 400, and thus, mixing of layers separated from each other by centrifugation will be reduced or prevented. Inner and outer gaps G1 and G2 of the bottleneck portion 401, that is, a gap between the bottleneck portion 401 and the top wall 1001 should have a size or dimension that is greater than a size or dimension of a gap that would induce a capillary phenomenon, so as to enable the flow of a fluid through the bottleneck portion 401 when it is desired. The fluid sample should be able to flow in the radial direction from the inner region 111 to the outer region 112 during centrifugation, and back and forth between the inner and outer regions 111, 112 during agitation to allow for mixing fine beads with target cells. If a capillary phenomenon occurs in the bottleneck portion 401, the bottleneck portion 401 would become blocked or clogged up, thereby making the flow of the fluid difficult during centrifugation and agitation. According to the present embodiment, the inner and outer gaps G1 and G2 of the bottleneck portion 401 have sizes or dimensions that are greater than a size or dimension of a gap that would induce the capillary phenomenon, and during centrifugation, the fluid smoothly moves from the inner region 111 to the outer region 112 due to the centrifugal force. After the centrifugation, the flow of the fluid between the inner region 111 and the outer region 112 may be partially restricted due to the relatively narrow inner and outer gaps G1 and G2. During mixing or agitation, the microfluidic apparatus 1 is rotated in clockwise and counterclockwise directions for a predetermined length of time. The fine beads and the target cells in the sample chamber 110 are mixed by moving back and forth between the inner region 111 and the outer region 112. The attachment of fine beads to the target cells may occur in both the inner and outer regions 111, 112 of the sample chamber 110. The gap G2 should allow the flow of target cells with attached fine beads (about 50 μm or less), white blood cells, red blood cells, target cell clusters (about 300 μm or less), and so on. For example, the size of the gap G2 may be in a rage of 0.5 mm~20 mm (more preferably 1 mm-20 mm for better performance). If the gap is too small, mixing of the beads may not be possible, or the efficiency of mixing may be reduced.

During centrifugation, the sample needs to smoothly flow from the inner region 111 to the outer region 112. In one embodiment, as illustrated in FIG. 12, the partition wall 400 is formed in such a way that the bottleneck portion 401 becomes narrower from an inner portion of the sample chamber 110 (e.g., region 111) toward an outer portion of the sample chamber 110 (e.g., region 112). That is, a fluid passage formed by the bottleneck portion 401 may have an outer gap G2 that is narrower than the inner gap G1. During centrifugation, the sample flows from the inner region 111 to the outer region 112 due to the centrifugal force, that is, the sample may pass through the bottleneck portion 401 from the wider inner gap G1 to the narrower inner gap G2 to reach the outer region 112. However, when centrifugation is stopped, the centrifugal force disappears. Accordingly, due to the narrow outer gap G2, the sample does not smoothly pass back through the bottleneck portion 401. Thus, during centrifugation, the sample may relatively smoothly flow from the inner region 111 to the outer region 112, and when centrifugation is stopped, a flow of the sample from the outer region 112 to the inner region 111 is reduced or restricted. The shape of a cross-section of the partition wall 400 for forming the bottleneck portion 401 may be triangle with an apex 404 as illustrated in FIG. 12. In this regard, an inclined angle A2 of a hypotenuse 406 of the outer region 112 is greater than an inclined angle A1 of a hypotenuse 405 of the inner region 111. Such a structure may easily restrict the flow of the sample from the outer region 112 to the inner region 111. In addition, since the hypotenuse 405 and the bottom surface 113 of the inner region 111 do not have a step therebetween, the sample may more smoothly flow from the inner region 111 to the outer region 112 during centrifugation. The shape of a cross-section of the partition wall 400 for forming the bottleneck portion 401 may take on other shapes, including curved shapes.

Figure 13:
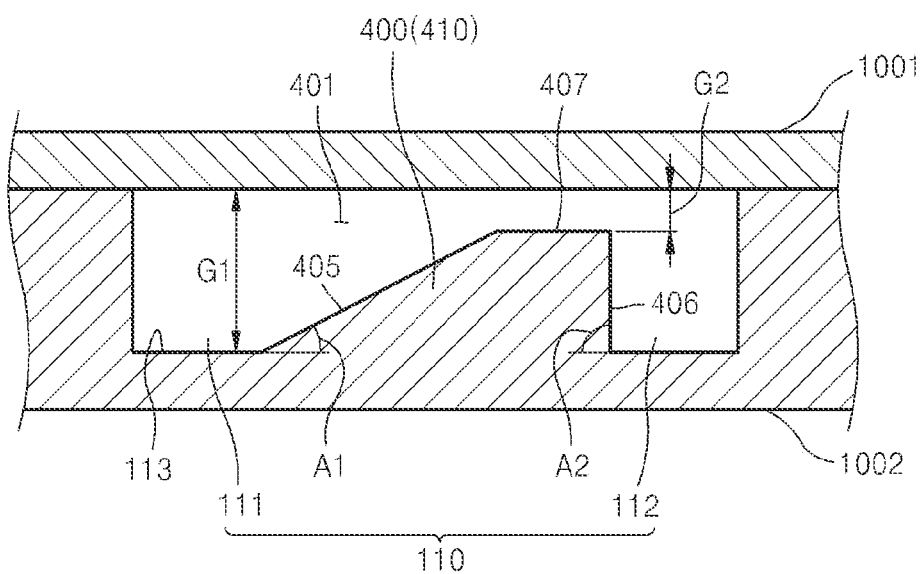
FIG. 13 is a cross-sectional view of an example of a bottle-neck portion.

Although the partition wall 400 illustrated in FIG. 12 has a triangular cross-section, embodiments are not limited thereto. As illustrated in FIG. 13, the cross-section of the partition wall 400 may be a trapezoid having the hypotenuses 405 and 406 and a top surface 407 parallel to the top wall 1001. In addition, the cross-section of the partition wall 400 may have various other shapes as long as a size or dimension of the minimal gap of the bottleneck portion 401 is greater than a size or dimension of a gap that would induce a capillary phenomenon.

For example, when blood containing circulating cancer cells is centrifuged in the sample chamber 110, a plasma layer, a white blood cell, and a circulating cancer cell layer, and a RBC layer are sequentially located in a direction from the inner portion to the outer portion of the sample chamber 110. The partition wall 400 may be located between the plasma layer and the white blood cell and circulating cancer cell layer. That is, the partition wall 400 may partition the sample chamber 110 in such a way that the plasma layer is located in the inner region 111 and the white blood cell and circulating cancer cell layer and the RBC layer are located in the outer region 112. According to another embodiment, the partition wall 400 may partition the sample chamber 110 in such a way that the hypotenuse 406 of the outer region 112 of the partition wall 410 is located between the plasma layer, and the white blood cell and circulating cancer cell layer. By doing so, a possibility for mixing the plasma layer containing a protein inhibiting the binding between a circulating cancer cell and fine beads with a layer containing a circulating cancer cell after centrifugation may decrease.

Figure 14:
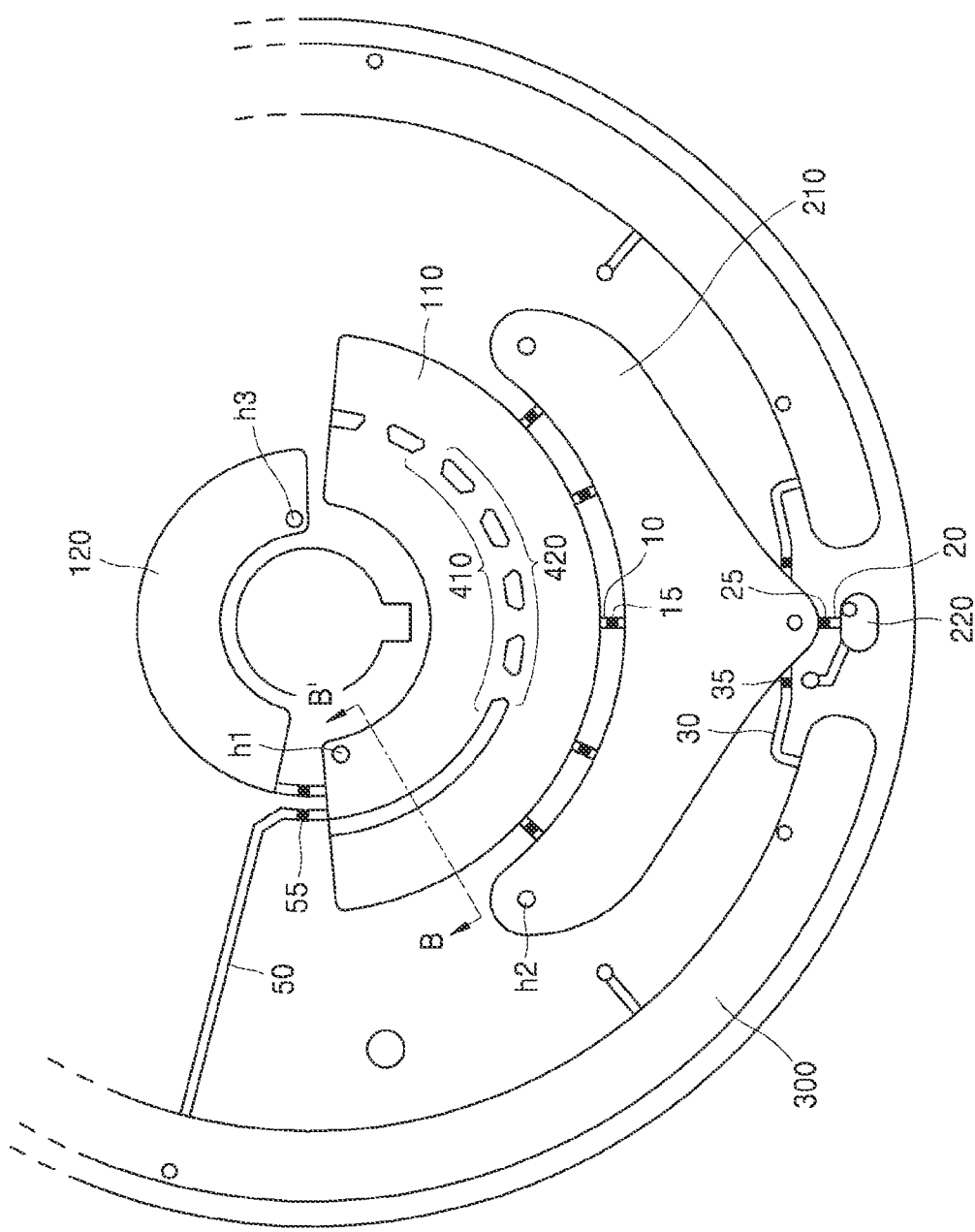
FIG. 14 is a plan view of a microfluidic apparatus including a partition wall disposed in a sample chamber, according to another embodiment.

FIG. 14 is a plan view of the microfluidic apparatus 1 according to an embodiment. Referring to FIG. 14, a plurality of partition walls 410 are spaced apart from each other in the circumference direction of the sample chamber 110 to form at least one opening 420 between the partition walls 410. A width of the opening 420 may be, for example, in a range of about 200 μm to 1 cm. The partition walls 410 may have identical lengths, and at least one of the partition walls 410 may have a length that is different from those of the other partition walls 410. For example, the partition walls 410 may extend from the bottom wall 1002 to the top wall 1001. Due to the partition walls 400, the sample chamber 110 is divided into an inner region 111, which is relatively close to the rotation center RC in the radial direction, and an outer region 112, which is relatively far from the rotation center RC in the radial direction. The opening 420 may connect the inner region 111 to the outer region 112.

As illustrated in FIG. 14, the opening 420 may be narrower from the inner portion to the outer portion of the sample chamber 110. Due to such a structure, the sample may relatively smoothly flow from the inner region 111 to the outer region 112, and a flow of the sample in the reverse direction thereof is reduced or restricted. Furthermore, at least one of the partition walls 410 may form the bottleneck portion 401 together with the top wall 1001 as illustrated in FIGS. 12 and 13. Although not illustrated in FIG. 14, the partition walls 410 may extend from the top wall 1001 to the bottom wall 1002 of the sample chamber 110. The partition walls 410 and the opening 420 may also be applied to the microfluidic apparatuses 1 of FIGS. 1B, 3, 4, 9, and 10.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A microfluidic apparatus adapted to be mounted on a rotation driving unit and wherein when mounted on the rotation driving unit and rotated about a rotation center of the apparatus, a fluid flow is induced in the apparatus due to a centrifugal force, the microfluidic apparatus comprising:
    a sample chamber in which a sample fluid is centrifuged,
    wherein a partition wall is provided in the sample chamber to form a bottleneck portion together with at least one of a top wall and a bottom wall of the sample chamber, wherein the partition wall defines an inner region and an outer region within the sample chamber, wherein the outer region is located further away along a radial direction from the rotation center than the inner region, and wherein the bottleneck portion partially restricts the flow of the sample fluid in a radial direction of the sample chamber through a gap region in the bottleneck portion, the gap region joining the inner region and the outer region within the sample chamber, and
    wherein the gap region has a size or dimension that is greater than a size or dimension of a gap that would induce a capillary phenomenon with the sample fluid and which is sufficiently large to allow target cells and fine beads in the sample fluid to move back and forth through the gap region between the inner region and the outer region within the sample chamber during a mixing process whereby the apparatus is rotated back and forth in clockwise and counterclockwise directions about the rotation center, and which partially restricts the flow of sample fluid in an inward radial direction from the outer region to the inner region within the sample chamber when the apparatus is not being rotated,
    wherein the partition wall has a shape wherein the bottleneck portion is narrower from the inner region of the sample chamber to the outer region of the sample chamber in the radial direction, and
    wherein the partition wall includes a plurality of partition wall segments arranged within the sample chamber along a circumference direction of the sample chamber, wherein the partition wall segments are spaced apart from each other along the circumference direction with an opening between adjacent partition wall segments.

2. The microfluidic apparatus of claim 1, wherein the partition wall is located within the sample chamber across an entire width of the sample chamber along the circumference direction of the sample chamber.

3. The microfluidic apparatus of claim 1, wherein the partition wall is located within the sample chamber across a portion of a width of the sample chamber in the circumference direction of the sample chamber.

4. The microfluidic apparatus of claim 1, wherein each of the openings is narrower from the inner region of the sample chamber to the outer region of the sample chamber in the radial direction.

5. A microfluidic apparatus adapted to be mounted on a rotation driving unit and wherein when mounted on the rotation driving unit and rotated about a rotation center of the apparatus, a fluid flow is induced in the apparatus due to a centrifugal force, the microfluidic apparatus comprising:
    a sample supplying unit having a sample chamber that houses a sample fluid including a fluid and a target material in which fine beads are bound to target cells;
    a density-gradient separation unit having a density-gradient separation chamber that houses a density gradient material with a lower density than the target material, wherein the density-gradient separation chamber is located farther away along a radial direction from the rotation center than the sample chamber;
    a fluid supplying channel that fluidly couples the sample supplying unit with the density-gradient separation unit; and
    a fluid supplying valve in the fluid supplying channel to selectively allow a flow of the sample fluid through the fluid supplying channel;
    wherein the density-gradient separation unit receives the sample fluid from the sample supplying unit and the target material is separated from the fluid based on density difference, and
    wherein the sample chamber includes a partition wall that forms a bottleneck portion together with at least one of a top wall and a bottom wall of the sample chamber, wherein the partition wall defines an inner region and an outer region within the sample chamber, wherein the outer region is located further away along a radial direction from the rotation center than the inner region, and wherein the bottleneck portion partially restricts flow of the sample fluid in a radial direction of the sample chamber through a gap region in the bottleneck portion, the gap region joining the inner region and the outer region within the sample chamber, and wherein the gap region has a size or dimension that is greater than a size or dimension of a gap that would induce a capillary phenomenon and which is sufficiently large to allow target cells and fine beads in the sample fluid to move back and forth through the gap region between the inner region and the outer region within the sample chamber during a mixing process whereby the apparatus is rotated back and forth in clockwise and counterclockwise directions about the rotation center, and which partially restricts the flow of sample fluid in an inward radial direction from the outer region to the inner region within the sample chamber when the apparatus is not being rotated, wherein the partition wall includes a plurality of the partition wall segments arranged within the sample chamber along a circumference direction of the sample chamber and wherein the partition wall segments are spaced apart from each other along the circumference direction with an opening between adjacent partition wall segments.

6. The microfluidic apparatus of claim 5, wherein the size or dimension of the gap region is between about 0.5 mm and about 20.0 mm.

7. The microfluidic apparatus of claim 5, wherein
the partition wall has a shape wherein the bottleneck portion is narrower from the inner region of the sample chamber to the outer region of the sample chamber in the radial direction of the sample chamber.

8. The microfluidic apparatus of claim 7, wherein
the partition wall is located within the sample chamber across a width of the sample chamber in a circumference direction of the sample chamber.

9. The microfluidic apparatus of claim 5, wherein
the partition wall is located within the sample chamber across a portion of a width of the sample chamber in a circumference direction of the sample chamber.

10. The microfluidic apparatus of claim 5, wherein
each of the openings is narrower from the inner region of the sample chamber to the outer region of the sample chamber in the radial direction.

11. The microfluidic apparatus of claim 5, wherein
the density-gradient separation unit comprises
a separation chamber that is coupled with the sample chamber by the fluid supplying channel and that houses the density gradient material,
a recovery chamber that is connected to the separation chamber by a recovery channel and that recovers the target material from the separation chamber, and
a recovery valve in the recovery channel to selectively control a flow of fluid through the recovery channel.

12. The microfluidic apparatus of claim 11, further comprising:
a waste chamber;
a discharge channel that is disposed on the separation chamber closer to the rotation center than the recovery channel in the radial direction and that fluidly couples the separation chamber with the waste chamber, to allow for discharge of a portion of fluid disposed above the target material from the separation chamber; and
a discharge valve in the discharge channel to control the flow of fluid through the discharge channel.

13. The microfluidic apparatus of claim 5, wherein
the sample supplying unit comprises a fine beads chamber housing the fine beads, a first channel fluidly coupling the sample chamber with the fine beads chamber, and a first valve in the first channel to selectively allow a flow of the fine beads into the sample chamber, and
wherein the density-gradient separation unit is fluidly coupled with the sample chamber.

14. The microfluidic apparatus of claim 13, wherein
the sample is separated into a plurality of layers due to a centrifugal force in the sample chamber, and
the layers comprise a target layer including the target cell and an upper material layer located above the target layer, and
wherein the microfluidic apparatus further comprises:
a waste chamber;
a second channel fluidly coupling the sample chamber with the waste chamber; and
a second valve for selectively opening the second channel,
wherein the upper material layer is discharged to the waste chamber through the second channel.

15. The microfluidic apparatus of claim 14, further including
a third valve in the second channel and located closer to the waste chamber than the second valve, so that when the upper material layer is discharged, the third valve closes the second channel.

16. The microfluidic apparatus of claim 15, further including
a fourth valve in the second channel to sequentially close and open the second channel.

17. The microfluidic apparatus of claim 5, further comprising
a lysis solution chamber for providing a lysis solution to lyse a particular cell in the sample.

18. The microfluidic apparatus of claim 5, wherein
the sample chamber houses the sample and a first density gradient material, and due to a centrifugal force, a target layer comprising the target cell is located above the first density gradient material, and
wherein the sample supplying unit further comprises a reaction chamber that receives fluid comprising the target layer from the sample chamber so that the fluid is mixed with the fine beads to form the target material.

19. The microfluidic apparatus of claim 5, wherein
the target cell includes a circulating tumor cell, a cancer stem cell, or a cancer cell.

20. The microfluidic apparatus of claim 5, wherein one or more of the partition wall segments, but not all of the partition wall segments, extends from the top wall to the bottom wall of the sample chamber.

21. The microfluidic apparatus of claim 1, wherein one or more of the partition wall segments, but not all of the partition wall segments, extends from the top wall to the bottom wall of the sample chamber.

* * * * *